(12) United States Patent
Boehme et al.

(10) Patent No.: US 8,901,114 B2
(45) Date of Patent: Dec. 2, 2014

(54) OXATHIAZINE DERIVATIVES SUBSTITUTED WITH CARBOCYCLES OR HETEROCYCLES, METHOD FOR PRODUCING SAME, DRUGS CONTAINING SAID COMPOUNDS, AND USE THEREOF

(75) Inventors: Thomas Boehme, Frankfurt am Main (DE); Christian Engel, Frankfurt am Main (DE); Stefan Guessregen, Frankfurt am Main (DE); Torsten Haack, Frankfurt am Main (DE); Gerhard Kretzschmar, Frankfurt am Main (DE); Kurt Ritter, Frankfurt am Main (DE); Georg Tschank, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/003,499

(22) PCT Filed: Mar. 7, 2012

(86) PCT No.: PCT/EP2012/053935
§ 371 (c)(1),
(2), (4) Date: Sep. 6, 2013

(87) PCT Pub. No.: WO2012/120052
PCT Pub. Date: Sep. 13, 2012

(65) Prior Publication Data
US 2013/0345128 A1 Dec. 26, 2013

(30) Foreign Application Priority Data
Mar. 8, 2011 (EP) .................................... 11305240

(51) Int. Cl.
| | | |
|---|---|---|
| *A61K 31/51* | (2006.01) | |
| *C07D 291/08* | (2006.01) | |
| *C07D 515/04* | (2006.01) | |
| *A61K 31/5415* | (2006.01) | |
| *A61K 31/55* | (2006.01) | |
| *A61K 31/69* | (2006.01) | |
| *A61K 45/06* | (2006.01) | |
| *C07D 419/12* | (2006.01) | |
| *C07F 5/02* | (2006.01) | |

(52) U.S. Cl.
CPC ............ *C07D 291/08* (2013.01); *C07D 515/04* (2013.01); *A61K 31/5415* (2013.01); *A61K 31/55* (2013.01); *A61K 31/69* (2013.01); *A61K 45/06* (2013.01); *C07D 419/12* (2013.01); *C07F 5/027* (2013.01)
USPC .......................... 514/222.5; 514/222.2; 544/2

(58) Field of Classification Search
None
See application file for complete search history.

(56) References Cited

U.S. PATENT DOCUMENTS

2013/0345125 A1* 12/2013 Boehme et al. ................ 514/6.5
2014/0024584 A1* 1/2014 Boehme et al. ................ 514/6.5

FOREIGN PATENT DOCUMENTS

WO  WO 02/11722 A1    2/2002
WO  WO 2008/073956 A2  6/2008

OTHER PUBLICATIONS

Seigo Suzue et al., Studies on Hypoglycemic Agents. IV. 1) Synthesis of 1,4,3-Benzoxathiazine-4,4-dioxides, Chemical and Pharmaceutical Bulletin, (May 25, 1968), vol. 16, No. 5, pp. 806-813.
Tsuneo Iwakawa et al., Cycloaddition in Synthesis of Sulfonamide Derivatives. IV. One-Pot Synthesis of 3-Dimethylamino-4,1,2-benzoxathiazine 1,1-Dioxides,3-Methoxy-4-methyl-1,2,4-benzothiadizine 1,1-Dioxiade and 3-Dimethylamino-1,4,2-benzodithiazine 1,1-Dioxides, Chemical and Pharmaceutical Bulletin, (Aug. 25, 1991), vol. 39, No. 8, pp. 1939-1943.
International Search Report dated Aug. 7, 2012 issued in PCT/EP2012/053935.

* cited by examiner

*Primary Examiner* — James H Alstrum Acevedo
*Assistant Examiner* — Fred Reynolds
(74) *Attorney, Agent, or Firm* — Scully, Scott, Murphy & Presser, P.C.

(57) ABSTRACT

The invention relates to the compounds of formula (I) and physiologically acceptable salts thereof. The compounds are suitable, e.g., for treating hyperglycemia.

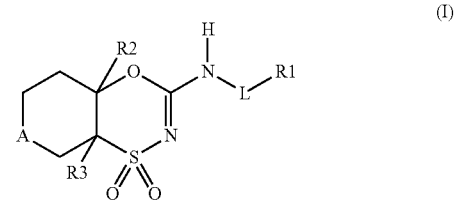

(I)

11 Claims, No Drawings

OXATHIAZINE DERIVATIVES SUBSTITUTED WITH CARBOCYCLES OR HETEROCYCLES, METHOD FOR PRODUCING SAME, DRUGS CONTAINING SAID COMPOUNDS, AND USE THEREOF

Oxathiazine derivatives substituted with carbocycles or heterocycles, method for producing same, drugs containing said compounds, and use thereof.

The invention relates to oxathiazine derivatives substituted by carbocycles or heterocycles, and to the physiologically compatible salts thereof.

It was an object of the invention to provide compounds which display a therapeutically utilizable action. More particularly, it was a further object to find novel compounds suitable for treatment of diabetes, hyperglycemia, insulin resistance, obesity, lipid metabolism disorders or other diseases.

The invention therefore relates to the compound of the formula I

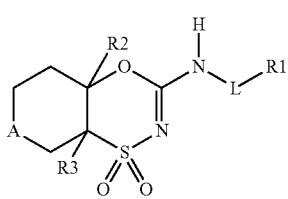

(I)

in which

A is a bond, $CH_1$, $CF_2$, O;
L is a bond, C(R5)(R6), N(R5);
R1 $(C_3-C_8)$-carbocycle,
  where the carbocycle radical may be mono- to trisubstituted by F, Cl, Br, I, OH, —$(C_1-C_6)$-alkylene-OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  $(C_6-C_{10})$-aryl,
  where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  4-12-membered heterocycle,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  and where the heterocycle may be fused to a further ring or ring system;
R2, R3 are each independently H, $(C_1-C_6)$-alkyl;
R5, R6 are each independently H, $(C_1-C_6)$-alkyl, $(C_3-C_8)$-cycloalkyl, $(C(R7)(R8))_n$-O—(CO)—N(R7)(R8);
R7, R8 are each independently H, $(C_1-C_6)$-alkyl;
n is 0, 1, 2;
and pharmaceutically acceptable salts thereof.

Preference is given to compounds of the formula I in which:
A is a bond, $CH_2$, $CF_2$;
L is a bond, C(R5)(R6), N(R5);
R1 $(C_3-C_8)$-carbocycle,
  where the carbocycle radical may be mono- to trisubstituted by F, Cl, Br, I, OH, —$(C_1-C_6)$-alkylene-OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  a heterocycle selected from the group of thiophene, pyran, tetrahydropyran, piperidine, thiopyran, tetrahydrothiopyran, pyrrole, tetrahydropyrrole, azepane or 2,3,4,5,6,7,8,9,10,11-decabora-bicyclo[8.1.1]dodecane,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, $(C_1-C_6)$-alkyl, $NH_2$, NH$(C_1-C_6)$-alkyl, N$((C_1-C_6)$-alkyl), $SO_2$—$CH_3$, $SO_2$—$NH_2$, $SO_2$—NH$(C_1-C_6)$-alkyl, $SO_2$—N$((C_1-C_6)$-alkyl$)_2$, COOH, COO—$(C_1-C_6)$-alkyl, $CONH_2$, CONH$(C_1-C_6)$-alkyl, CON$((C_1-C_6)$-alkyl$)_2$, $SF_5$;
  and where the heterocycle may be fused to a further ring or ring system;
R2, R3 are each independently H, $(C_1-C_6)$-alkyl;
R5, R6 are each independently H, $(C_3-C_8)$-cycloalkyl, $(C_1-C_6)$-alkylene-$(C_3-C_8)$-cycloalkylene, $(C(R7)(R8))_n$-O—(CO)—N(R7)(R8);
R7, R8 are each independently H, $(C_1-C_6)$-alkyl;
n is 0, 1, 2;
and pharmaceutically acceptable salts thereof.

Particular preference is given to compounds of the formula I in which
A is a bond, $CH_2$, $CF_2$;
L is a bond, C(R5)(R6), N(R5);
R1 $(C_3-C_8)$-carbocycle,
  where the carbocycle radical may be mono- to trisubstituted by F, Cl, Br, I, OH, —$(C_1-C_6)$-alkylene-OH, $CF_3$, $NO_2$, CN, $OCF_3$, $(C_1-C_6)$-alkyl, $CONH_2$, CONH$(C_1-C_6)$-alkyl, CON$((C_1-C_6)$-alkyl$)_2$;
  phenyl,
  where the phenyl radical may be mono- to trisubstituted by F, Cl, Br, I, OH, —$(C_1-C_6)$-alkylene-OH, $CF_3$, $NO_2$, CN, $OCF_3$, $(C_1-C_6)$-alkyl, $CONH_2$, CONH$(C_1-C_6)$-alkyl, CON$((C_1-C_6)$-alkyl$)_2$;
  a heterocycle selected from the group of carborane, thiophene, tetrahydropyran, piperidine, thiochromane, hexahydrocyclopenta[c]pyrrole, azepane and 2,3,4,5,6,7,8,9,10,11-decaborabicyclo[8.1.1]dodecane, where the heterocycle radical may be mono- to trisubstituted by F, Cl, Br, I, OH, —$(C_1-C_6)$-alkylene-OH, $CF_3$, $NO_2$, CN, $OCF_3$, $(C_1-C_6)$-alkyl, $CONH_2$, CONH$(C_1-C_6)$-alkyl, CON$((C_1-C_6)$-alkyl$)_2$;
R2, R3 are each independently H, $(C_1-C_6)$-alkyl;
R5, R6 are each independently H, $(C_1-C_6)$-alkyl;

and pharmaceutically acceptable salts thereof.

In one embodiment, preference is given to compounds of the formula I in which A is a bond.

In one embodiment, preference is given to compounds of the formula I in which A is $CH_2$.

In one embodiment, preference is given to compounds of the formula I in which A is $CF_2$.

In one embodiment, preference is given to compounds of the formula I in which A is O.

In one embodiment, preference is given to compounds of the formula I in which L is a bond.

In one embodiment, preference is given to compounds of the formula I in which L is C(R5)(R6).

In one embodiment, preference is given to compounds of the formula I in which L is N(R5).

In one embodiment, preference is given to compounds of the formula I in which R1 is $(C_3-C_8)$-carbocycle.

In one embodiment, preference is given to compounds of the formula I in which R1 is $(C_6-C_{10})$-aryl.

In one embodiment, preference is given to compounds of the formula I in which R1 is 4-12-membered heterocycle.

If radicals or substituents occur more than once in the compounds of the formula I (for example R7), they may each independently be defined as specified and be the same or different.

The invention relates to compounds of the formula I in the form of their tautomers, racemates, racemic mixtures, stereoisomer mixtures, pure stereoisomers, diastereoisomer mixtures and pure diastereoisomers. The mixtures are separated, for example, by a chromatographic route.

Because of their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, likewise belong within the framework of the invention as useful intermediates for the preparation or purification of pharmaceutically acceptable salts and/or for use in nontherapeutic, for example in vitro, applications.

The inventive compounds may also be in various polymorphic forms, for example as amorphous and crystalline polymorphic forms. All polymorphic forms of the inventive compounds are within the scope of the invention and are a further aspect of the invention.

All references to "compound(s) of formula I" hereinafter refer to compound(s) of the formula I as described above, and the salts and solvates thereof as described herein.

An alkyl radical is understood to mean a straight-chain or branched hydrocarbyl chain having one to eight carbons, for example methyl, ethyl, isopropyl, tert-butyl, hexyl, heptyl, octyl. The alkyl radicals may be mono- or polysubstituted as described above.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above.

Heterocycle and heterocyclic radical are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring or ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydro-benzothiazol-2-yl, 4,5,6,7-tetrahydrobenzoimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The compound(s) of the formula I can also be administered in combination with further active ingredients.

The amount of a compound of the formula I required to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other constituents of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination products are:

All antidiabetics mentioned in the Rote Liste 2009, chapter 12; all weight-reducing agents/appetite suppressants mentioned in the Rote Liste 2009, chapter 1; all diuretics mentioned in the Rote Liste 2009, chapter 36; all lipid-lowering agents mentioned in the Rote Liste 2009, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), Humulin®, VIAject™, or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® Insulin (MannKind) or Cobalamin™ oral insulin, or insulins as described in WO2007128815, WO2007128817, or insulins which can be administered transdermally; GLP-1 derivatives and GLP-1 agonists, for example exenatide, liraglutide, or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (Symlin; Amylin Pharmaceuticals), AVE-0010, BIM-51077 (R-1583, ITM-077), PC-DAC:Exendin-4 (an exendin-4 analog which is bonded covalently to recombinant human albumin), CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists, as described, for example, in D. Chen et al., Proc.

Natl. Acad. Sci. USA 104 (2007) 943, those as described in WO2006124529, WO2007124461, peptides, for example obinepitide (TM-30338), amylin receptor agonists, as described, for example, in WO2007104789, analogs of the human GLP-1, as described in WO2007120899, and orally active hypoglycemic ingredients.

Antidiabetics also include agonists of the glucose-dependent insulinotropic polypeptide (GIP) receptor, as described, for example, in WO2006121860.

Antidiabetics also include analogs and derivatives of fibroblast growth factor 21 (FGF-21).

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, or those as described in R. D. Carr et al., Diabetes 52, 2003, 2513-2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells,
inhibitors of dipeptidyl peptidase-IV (DPP-IV),
insulin sensitizers,
inhibitors of liver enzymes involved in stimulating gluconeogenesis and/or glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) antagonists,
fibrates,
cholesterol reabsorption inhibitors,
CETP inhibitors,
bile acid absorption inhibitors,
MTP inhibitors,
estrogen receptor gamma agonists (ERR agonists),
sigma-1 receptor antagonists,
antagonists of the somatostatin 5 receptor (SSTS receptor);
compounds which reduce food intake, and
compounds which increase thermogenesis.

In one embodiment of the invention, the compound of the formula I is administered in combination with insulin.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride.

In one embodiment, the compound of the formula I is administered in combination with a tablet which comprises both glimepiride, which is released rapidly, and metformin, which is released over a longer period (as described, for example, in US2007264331).

In one embodiment, the compound of the formula I is administered in combination with a biguanide, for example metformin.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008.

In one embodiment, the compound of the formula I is administered in combination with a thiazolidinedione, for example troglitazone, ciglitazone, pioglitazone, rosiglitazone or the compounds disclosed in WO 97/41097 to Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with a PPAR gamma agonist, for example rosiglitazone, pioglitazone, JTT-501, G1 262570, R-483, CS-011 (rivoglitazone), DRL-17564, DRF-2593 (balaglitazone), or those as described in WO2007060992, WO2007100027, WO2007103252, WO2007122970.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, CKD-501 (lobeglitazone sulfate), MBX-213, or as described in WO 00/64888, WO 00/64876, WO03/020269, WO2007099553, US2007276041, WO2007085135, WO2007085136, or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172, WO2007039178, WO2007071766, WO2007101864, US2007244094, WO2007119887.

In one embodiment of the invention, the compound of the formula I is administered in combination with a pan-SPPARM (selective PPAR modulator alpha, gamma, delta), for example GFT-505.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504 or as described in WO2004100875, WO2005065680, WO2006086488, WO2007106181, WO2007111864, WO2007120270, WO2007120284, WO2007123581, WO2007136577.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942.

In one embodiment, the compound of the formula I is administered in combination with an inhibitor of gluconeogenesis, for example FR-225654.

In one embodiment, the compound of the formula I is administered in combination with inhibitors of fructose 1,6-bisphosphatase (FBPase), for example CS-917 (MB-06322) or MB-07803, or those as described in WO2006023515, WO2006104030, WO2007014619, WO2007137962.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase IV (DPP-IV), for example vildagliptin (LAF-237), sitagliptin (MK-0431), sitagliptin phosphate, saxagliptin ((BMS-477118), GSK-823093, PSN-9301, SYR-322, SYR-619, TA-6666, TS-021, GRC-8200, GW-825964X, KRP-104, DP-893, ABT-341, ABT-279 or another salt thereof, S-40010, S-40755, PF-00734200, BI-1356, PHX-1149, alogliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, WO2007015767 (LY-2463665), WO2007024993, WO2007029086, WO2007063928, WO2007070434, WO2007071738, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a substance which enhances insulin secretion, for example KCP-265 (WO2003097064), or those as described in WO2007026761.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 or 2 (SGLT1, SGLT2), for example KGA-2727, T-1095, SGL-0010, AVE 2268, SAR 7226, SGL-5083, SGL-5085, SGL-5094, ISIS-388626, sergliflozin or dapagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, or by A. L. Handlon in Expert Opin. Ther. Patents (2005) 15(11), 1531-1540.

In one embodiment, the compound of the formula I is administered in combination with inhibitors of 11-beta-hydroxysteroid dehydrogenase 1 (11β-HSD1), for example BVT-2733, NJ-25918646, INCB-13739, D10-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427.

In one embodiment, the compound of the formula I is administered in combination with inhibitors of protein tyrosine phosphatase 1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058.

In one embodiment of the invention, the compound of the formula I is administered in combination with an agonist of GPR109A (HM74A receptor agonists; NAR agonists (nicotinic acid receptor agonists)), for example nicotinic acid or "extended release niacin" in conjunction with MK-0524A (laropiprant) or MK-0524, or those compounds as described in WO2006045565, WO2006045564, WO2006069242, WO2006085108, WO2006085112, WO2006085113, WO2006124490, WO2006113150, WO2007017261, WO2007017262, WO2007017265, WO2007015744, WO2007027532, WO2007092364, WO2007120575, WO2007134986.

In another embodiment of the invention, the compound of the formula I is administered in combination with a solid combination of niacin with simvastatin.

In another embodiment of the invention, the compound of the formula I is administered in combination with nicotinic acid or extended release niacin in conjunction with MK-0524A (laropiprant).

In a further embodiment of the invention, the compound of the formula I is administered in combination with nicotinic acid or extended release niacin in conjunction with MK-0524A (laropiprant) and with simvastatin.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572.

In one embodiment, the compound of the formula I is administered in combination with GPR119b modulators, as described, for example, in WO2004041274.

In one embodiment, the compound of the formula I is administered in combination with modulators of GPR119 (G protein-coupled glucose-dependent insulinotropic receptor), for example PSN-119-1, or those as described, for example, in WO2005061489 (PSN-632408), WO2004065380, WO2006018662, WO2007003960-62 and WO2007003964, WO2007116229, WO2007116230.

In a further embodiment, the compound of the formula I is administered in combination with modulators of GPR120, as described, for example, in EP1688138.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of serum/glucocorticoid-regulated kinase (SGK), as described, for example, in WO2006072354, WO2007093264.

In one embodiment, the compound of the formula I is administered in combination with an inhibitor of protein kinase C beta (PKC beta), for example ruboxistaurin.

In a further embodiment, the compound of the formula I is administered in combination with an activator of the AMP-activated protein kinase (AMPK), as described, for example, in WO2007062568.

In one embodiment, the compound of the formula I is administered in combination with an inhibitor of ceramide kinase, as described, for example, in WO2007112914.

In a further embodiment, the compound of the formula I is administered in combination with an inhibitor of MAPK-interacting kinase 2 (MNK2), as described, for example, in WO2007104053, WO2007115822.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, L-659699, or those as described in US2007249583.

In a further embodiment of the invention, the compound of the formula I is administered in combination with a farnesoid X receptor (FXR) antagonist, as described, for example, in WO2007052843, WO2007070796, WO2007092751, JP2007230909, WO2007095174, WO2007140174, WO2007140183.

In another embodiment of the invention, the compound of the formula I is administered in combination with a ligand of the liver X receptor (LXR), as described, for example, in WO2007092965.

In one embodiment of the invention, the compound of the formula I is administered in combination with a fibrate, for example fenofibrate, clofibrate, bezafibrate.

In one embodiment of the invention, the compound of the formula I is administered in combination with fibrates, for example the choline salt of fenofibrate (SLV-348).

In one embodiment of the invention, the compound of the formula I is administered in combination with fibrates, for example the choline salt of fenofibrate and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin or atorvastatin.

In a further embodiment of the invention, the compound of the formula I is administered in combination with Synordia (R), a solid combination of fenofibrate with metformin.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. Nos. 6,992,067 or 7,205,290.

In a further embodiment of the invention, the further active ingredient is a diphenylazetidinone derivative, as described, for example, in U.S. Pat. Nos. 6,992,067 or 7,205,290, combined with a statin, for example simvastatin, fluvastatin, pravastatin, lovastatin, cerivastatin, atorvastatin or rosuvastatin.

In one embodiment of the invention, the compound of the formula I is administered in combination with a solid combination of lapaquistat, a squalene synthase inhibitor, with atorvastatin.

In one embodiment of the invention, the compound of the formula I is administered in combination with a CETP inhibitor, for example torcetrapib, anacetrapib or JTT-705, or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906.

In one embodiment of the invention, the compound of the formula I is administered in combination with bile acid reabsorption inhibitor (see, for example, U.S. Pat. No. 6,245,744, U.S. Pat. No. 6,221,897 or WO00/61568), for example HMR 1741, or those as described in DE 10 2005 033099.1 and DE 10 2005 033100.9, WO2007009655-56.

In one embodiment, the compound of the formula I is administered in combination with agonists of GPBAR1 (G-protein-coupled bile acid receptor-1; TGR5), as described, for example, in WO2007110237, WO2007127505.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with a chewing gum comprising phytosterols (Reductol™)

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, or those as described in WO2005085226, WO2005121091, WO2006010423, WO2006113910.

In another embodiment of the invention, the compound of the formula I is administered in combination with an antagonist of the somatostatin 5 receptor (SSTS receptor), for example those as described in WO2006094682.

In one embodiment of the invention, the compound of the formula I is administered in combination with an ACAT inhibitor, for example avasimibe, SMP-797 or KY-382.

In a further embodiment of the invention, the compound of the formula I is administered in combination with an inhibitor of liver carnitine palmitoyltransferase 1 (L-CPT1), as described, for example, in WO2007063012, WO2007096251 (ST-3473).

In one embodiment of the invention, the compound of the formula I is administered in combination with a squalene synthetase inhibitor, for example BMS-188494, TAK-475 (lapaquistat acetate), or as described in WO2005077907, JP2007022943.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment of the invention, the compound of the formula I is administered in combination with an ABCA1 expression enhancer, as described, for example, in WO2006072393.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923.

In one embodiment of the invention, the compound of the formula I is administered in combination with an adenosine A2B receptor antagonist (adenosine A2B R), as described in US2007270433.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833).

In a further embodiment, the compound of the formula I is administered in combination with modulators of xanthine oxidoreductase (XOR).

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A);

NPY-5 receptor antagonists, such as L-152804 or the compound "NPY-5-BY" from Banyu, or as described, for example, in WO2006001318, WO2007103295, WO2007125952;

NPY-4 receptor antagonists, as described, for example, in WO2007038942;

NPY-2 receptor antagonists, as described, for example, in WO2007038943;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166;

derivatives of the peptide obestatin, as described by WO2006096847;

CB1R (cannabinoid receptor 1) antagonists, for example rimonabant, surinabant (SR147778), SLV-319, AVE-1625, taranabant (MK-0364) or salts thereof, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136607, WO2007136571, US7297710, WO2007138050, WO2007140385, WO2007140439;

cannabinoid receptor 1/cannabinoid receptor 2 (CB1/CB2) modulating compounds, for example delta-9-tetrahydrocannabivarin, or those as described, for example, in WO2007001939, WO2007044215, WO2007047737, WO2007095513, WO2007096764, WO2007112399, WO2007112402;

modulators of FAAH (fatty acid amide hydrolase), as described, for example, in WO2007140005;

vanilloid 1 receptor modulators (modulators of TRPV 1), as described, for example, in WO2007091948, WO2007129188, WO2007133637;

activators of the capsaicin receptor, as described, for example, in JP2007210969;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763;

orexin receptor 1 antagonists (OX1R antagonists), orexin receptor 2 antagonists (OX2R antagonists) or mixed OX1R/OX2R antagonists (e.g. 1-(2-methyl-benzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374; WO2007122591, WO2007126934, WO2007126935);

histamine H3 receptor antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893, US2005171181 (e.g. PF-00389027), WO2006107661, WO2007003804, WO2007016496, WO2007020213, WO2007049798, WO2007055418, WO2007057329, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111);

histamine H1/histamine H3 modulators, for example betahistine or its dihydrochloride;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756);

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]-ethanol hydrochloride (WO 01/83451) or solabegron (GW-427353) or N-5984 (KRP-204), or those as described in JP2006111553, WO2002038543, WO2002038544, WO2007048840-843;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916);

CCK-A (CCK-1) agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034, WO2007120655, WO2007120688, WO2007120718;

serotonin reuptake inhibitors (for example dexfenfluramine);

mixed serotonin/dopamine reuptake inhibitors (e.g. bupropion), or solid combinations of bupropion with naltrexone or bupropion with zonisamide;

mixed reuptake inhibitors, for example DOV-21947;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213);

5-HT6 receptor modulators, for example E-6837, BVT-74316 or PRX-07034, or those as described, for example, in WO2005058858, WO2007054257, WO2007107373, WO2007108569, WO2007108742-744;

agonists of estrogen receptor gamma (ERR agonists), as described, for example, in WO2007131005;

sigma-1 receptor antagonists, as described, for example, in WO2007098953, WO2007098961;

muscarin 3 receptor (M3R) antagonists, as described, for example, in WO2007110782; bombesin receptor agonists (BRS-3 agonists);

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457;

growth hormone secretagogue receptor modulators, for example JMV-2959, JMV-3002, JMV-2810, JMV-2951, or those as described in WO2006012577 (e.g. YIL-781 or YIL-870), WO2007079239;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

dopamine agonists (DA agonists, for example bromocriptine, Doprexin);

lipase/amylase inhibitors (e.g. WO 00/40569);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311;

inhibitors of fatty acid synthase (FAS), for example C75, or those as described in WO2004005277;

inhibitors of stearoyl-CoA delta9 desaturase (SCD1), as described, for example in WO2007009236, WO2007044085, WO2007046867, WO2007046868, WO20070501124, WO2007056846, WO2007071023, WO2007130075, WO2007134457, WO2007136746;

inhibitors of "adipocyte fatty acid-binding protein aP2", for example BMS-309403; activators of adiponectin secretion, as described, for example, in WO2006082978; promoters of adiponectin production, as described, for example, in WO2007125946;

oxyntomodulin;

oleoyl-estrone or agonists or partial agonists of the thyroid hormone receptor (thyroid hormone receptor agonists), for example: KB-2115, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864;

or agonists of the thyroid hormone receptor beta (TR-beta), for example MB-07811 or MB-07344.

In one embodiment of the invention, the compound of the formula I is administered in combination with an inhibitor of site-1 protease (S1P), for example PF-429242.

In a further embodiment of the invention, the compound of the formula I is administered in combination with an RNAi therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, succinobucol, probucol, tocopherol, ascorbic acid, β-carotene or selenium.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment, the compound of the formula I is administered in combination with an inhibitor of carboanhydrase type 2 (carbonic anhydrase type 2), for example those as described in WO2007065948.

In another embodiment, the compound of the formula I is administered in combination with topiramat.

In a further embodiment, the compound of the formula I is administered in combination with a solid combination of topiramat with phentermine (Qnexa™)

In a further embodiment, the compound of the formula I is administered in combination with an antisense compound, e.g. ISIS-377131, which inhibits the production of the glucocorticoid receptor.

In one embodiment, the compound of the formula I is administered in combination with an agonist of the RUP3 receptor, as described, for example, in WO2007035355.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463.

In one embodiment, the compound of the formula I is administered in combination with a "c-Jun N-terminal kinase" inhibitor (JNK inhibitor), as described, for example, in WO2007125405.

In one embodiment, the compound of the formula I is administered in combination with an endothelin A receptor antagonist, for example avosentan (SPP-301).

In one embodiment, the compound of the formula I is administered in combination with modulators of the glucocorticoid receptor (GR), for example KB-3305 or those compounds as described, for example, in WO2005090336, WO2006071609, WO2006135826, WO2007105766.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1 (an NAD$^+$-dependent protein deacetylase); this active ingredient may, for example, be resveratrol in suitable formulations, or those compounds as specified in WO2007019416 (e.g. SRT-1720).

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2007107587, WO2007111994.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is meterleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermin.

In a further embodiment, the further active ingredient is geniposidic acid (WO2007100104).

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

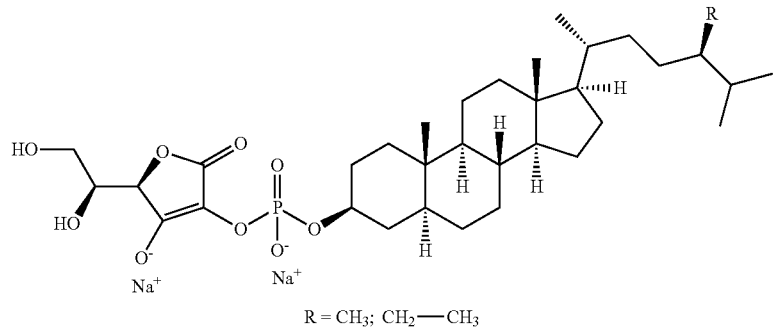

FM-VP4

R = CH$_3$; CH$_2$—CH$_3$

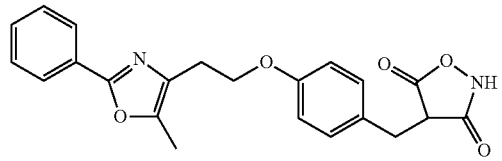

JTT-501

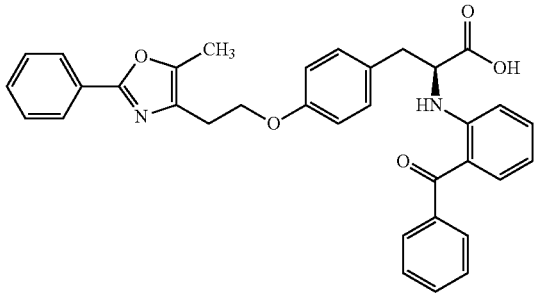

GI262570

-continued
CS-011
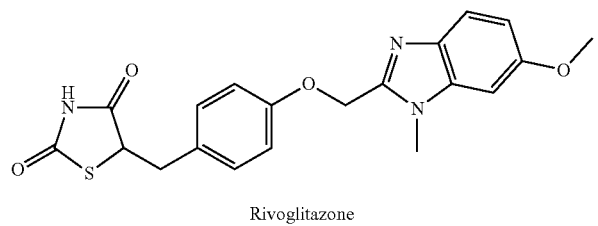
Rivoglitazone
GW-9578
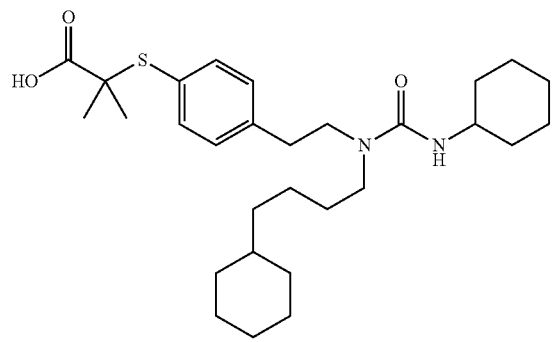
K-111
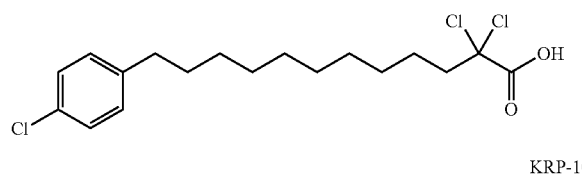
LY-518674
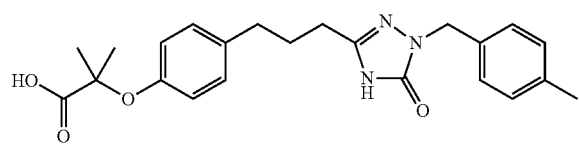
KRP-101
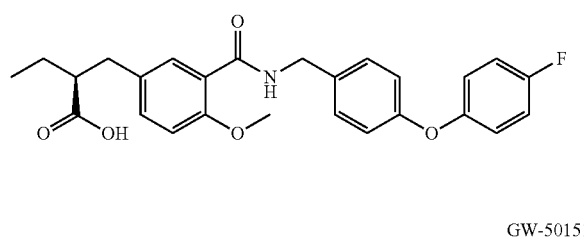
LY-510929
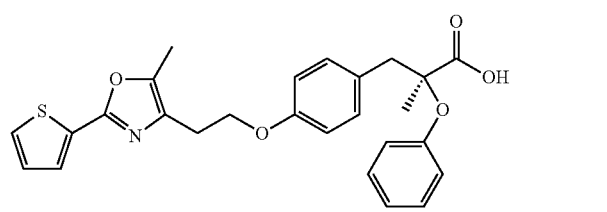
GW-501516
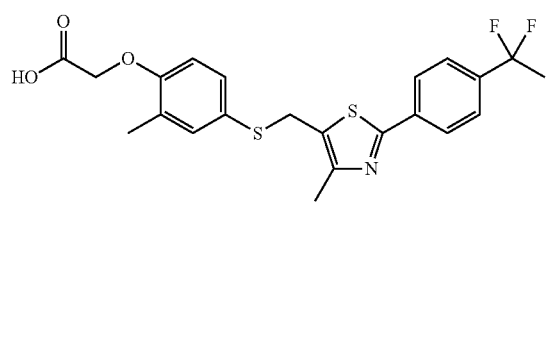
BMS-201038
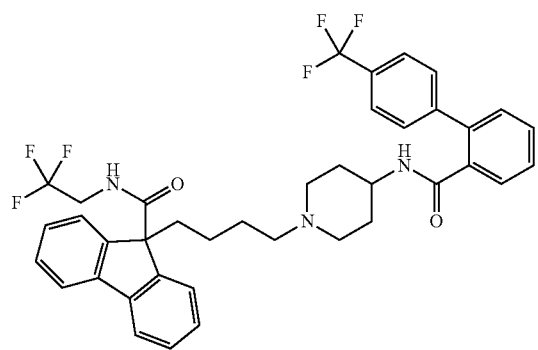
R-103757
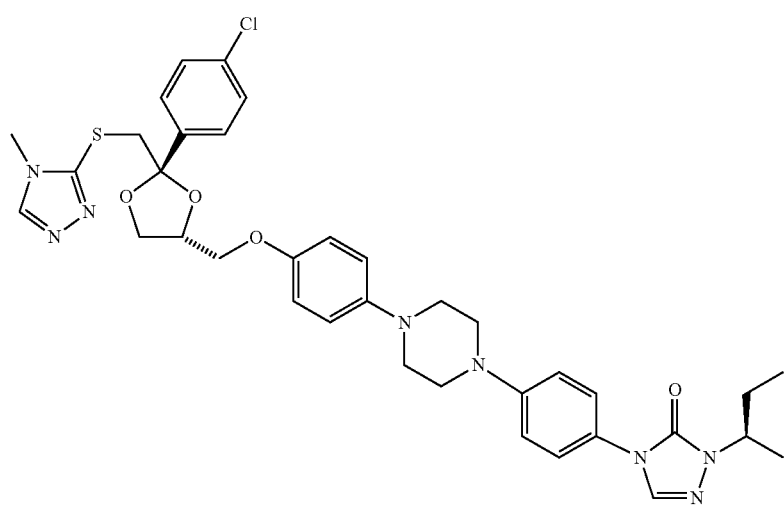

JTT-705
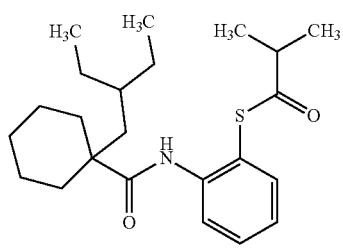
OPC-14117
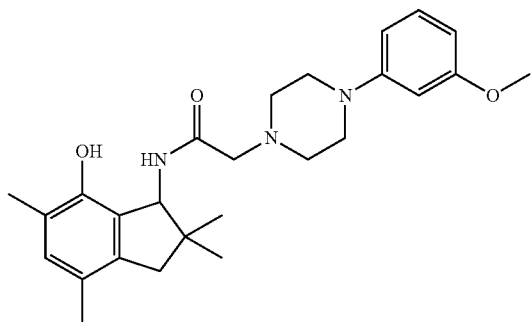
NO-1886
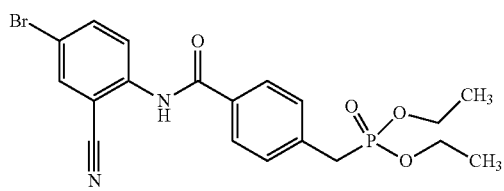
SB-204990
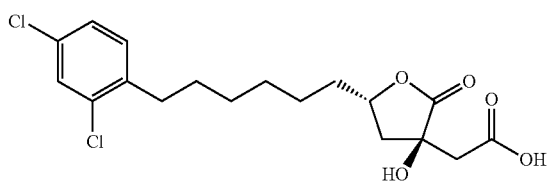
BMS-188494
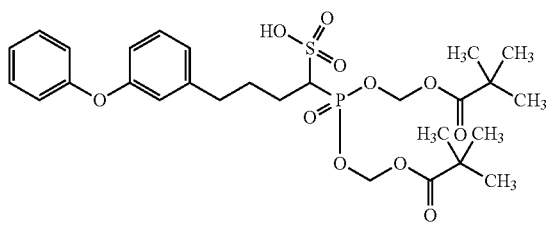
CI-1027
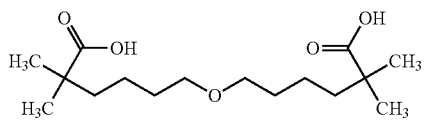
ATL-962
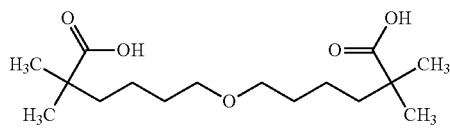
FR-258900
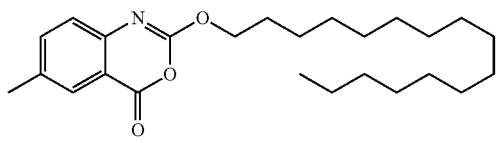
NNC-25-2504
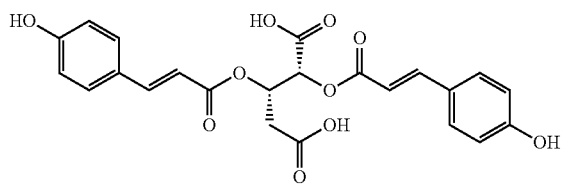
LY-2121260
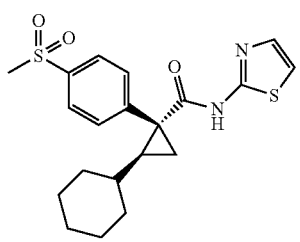
GKA-50
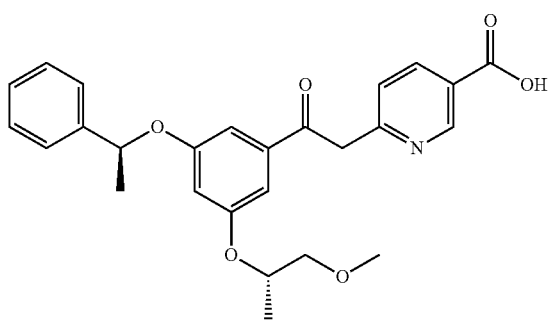
FR-225654
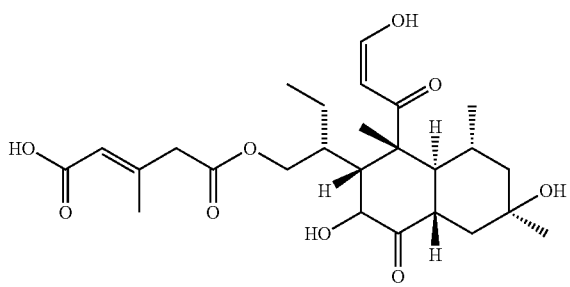

-continued
KST-48
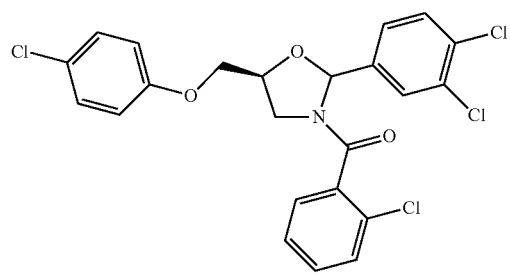
BMS-477118
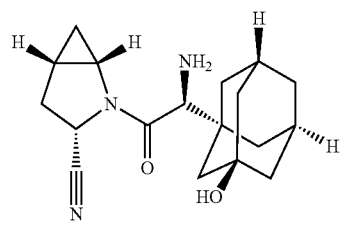
BVT-2733
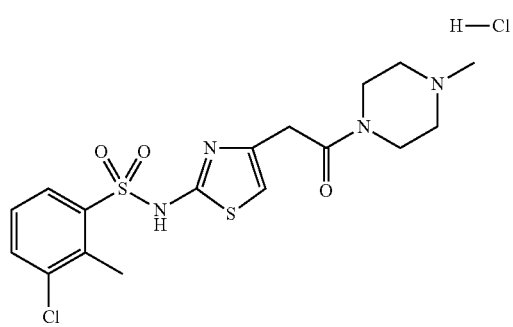
T-1095
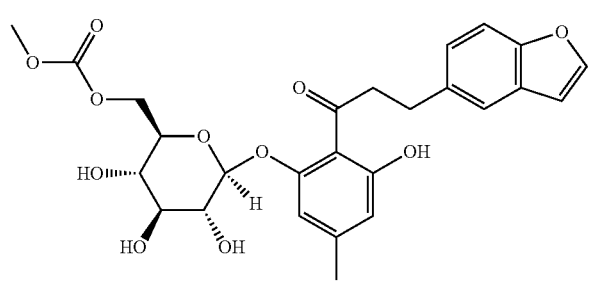
SPP-301
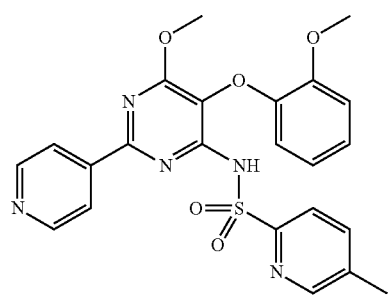
THIQ
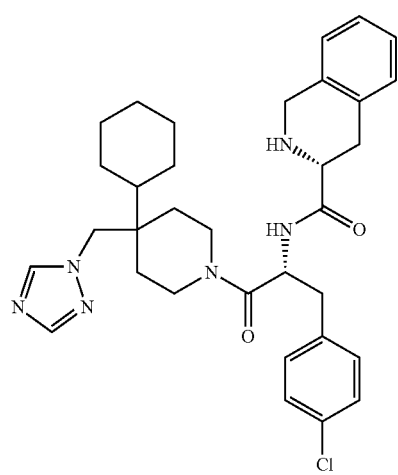
MB243
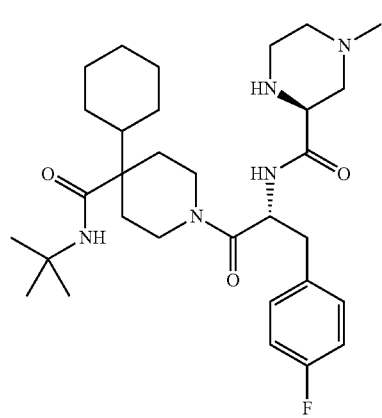
RY764
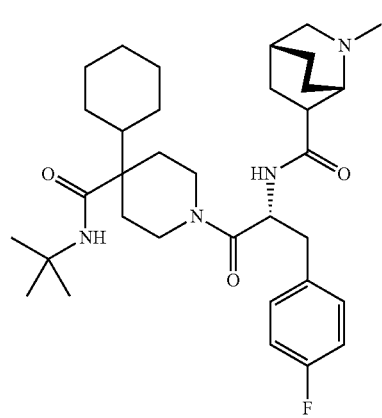

-continued
CHIR-785
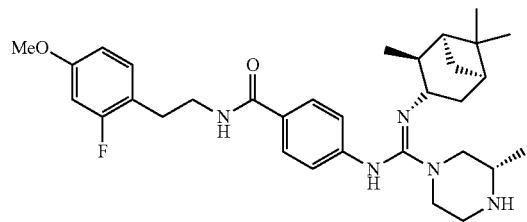
A-761
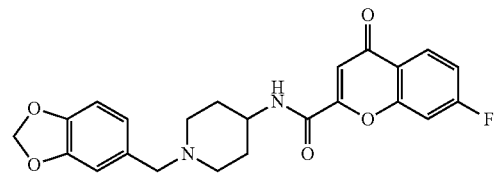
A-665798
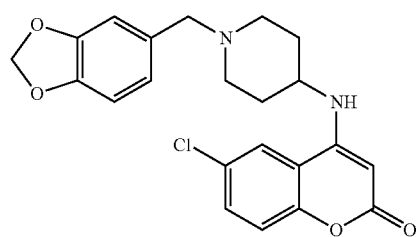
ATC-0175
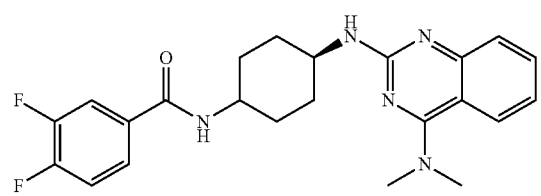
T-226296
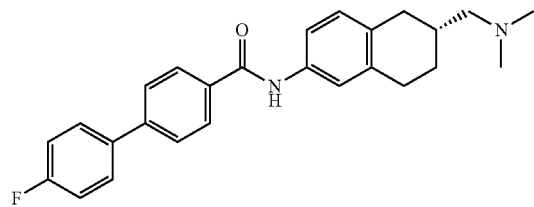
GW-803430
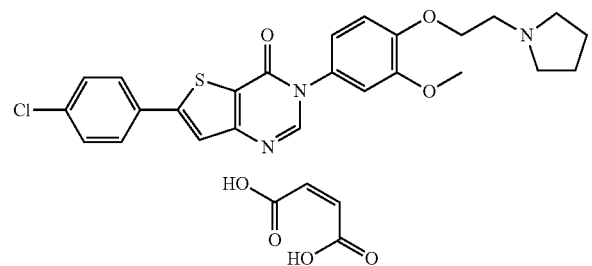
AOD-9604
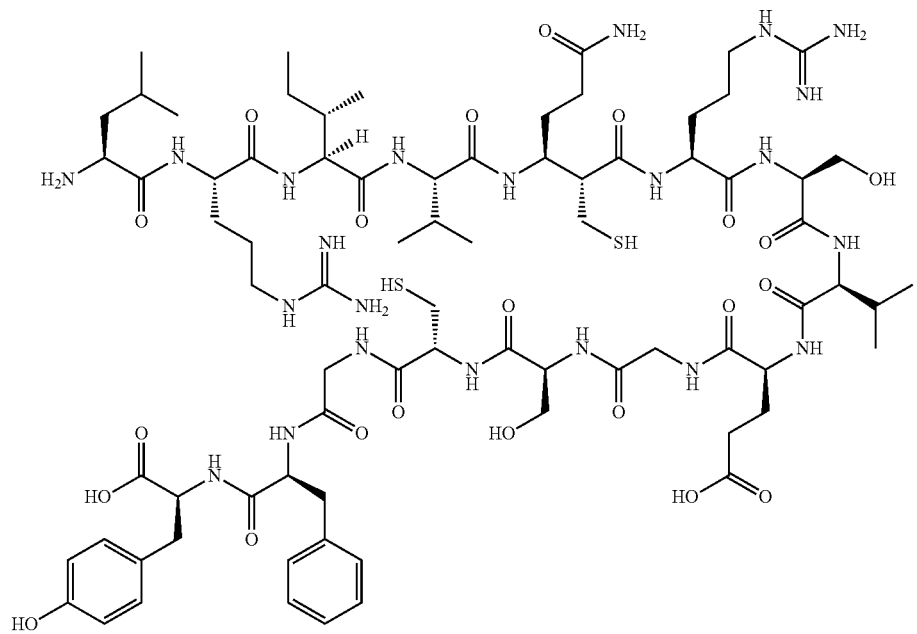

-continued
A-778193
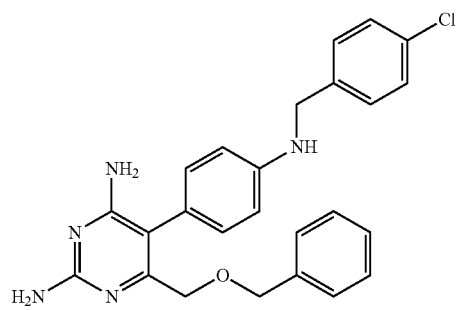
C75
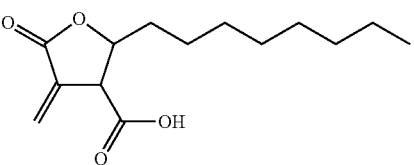
Oleoyl-Estron
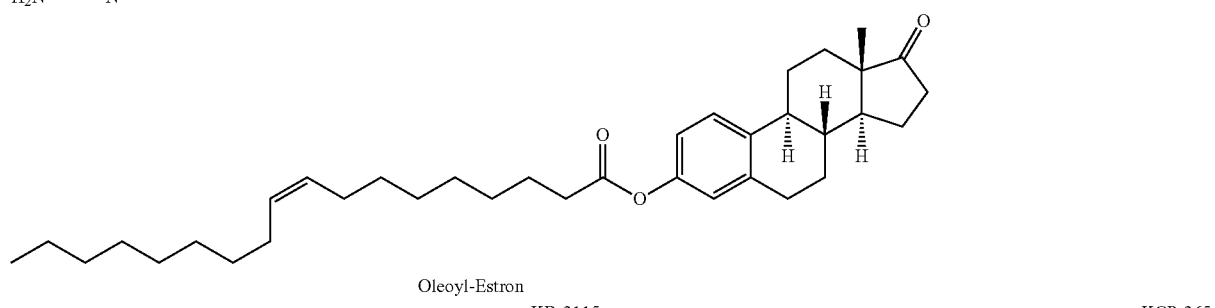
KB-2115
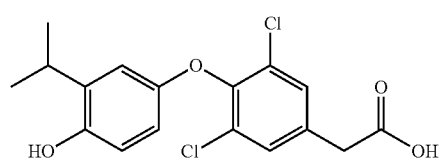
KCP-265
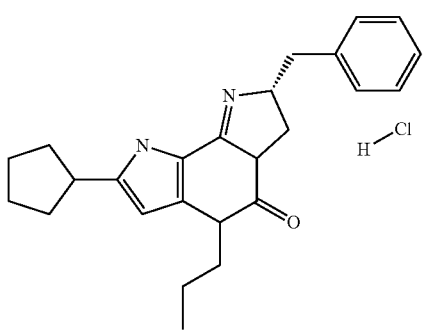
SMP-797
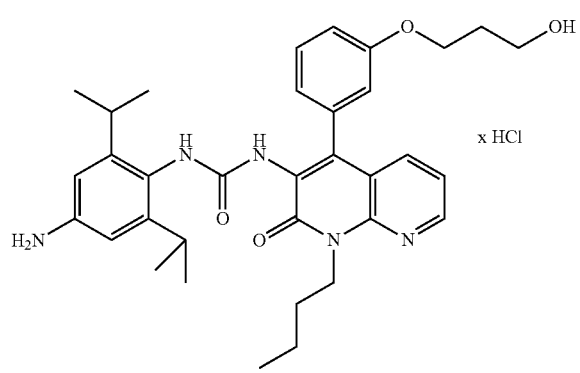 x HCl
JNJ-25918646
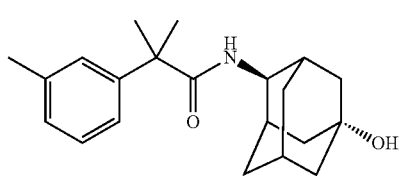
PSN-632408
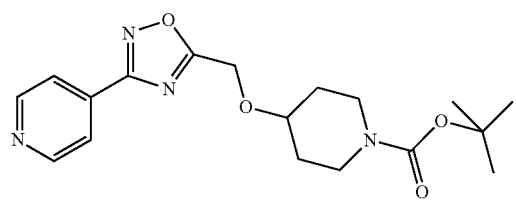
SYR-322
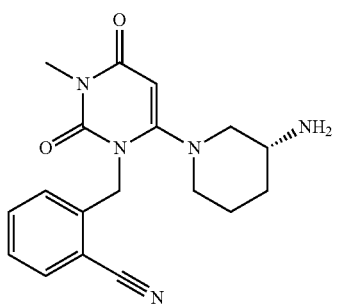

-continued
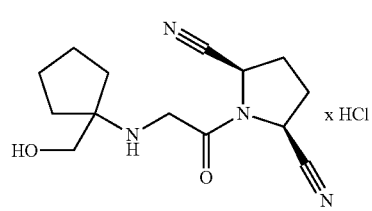
DP-893
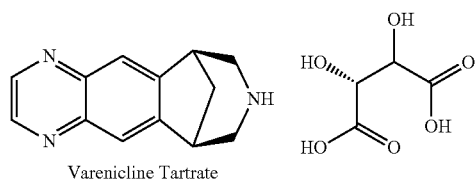
Varenicline Tartrate
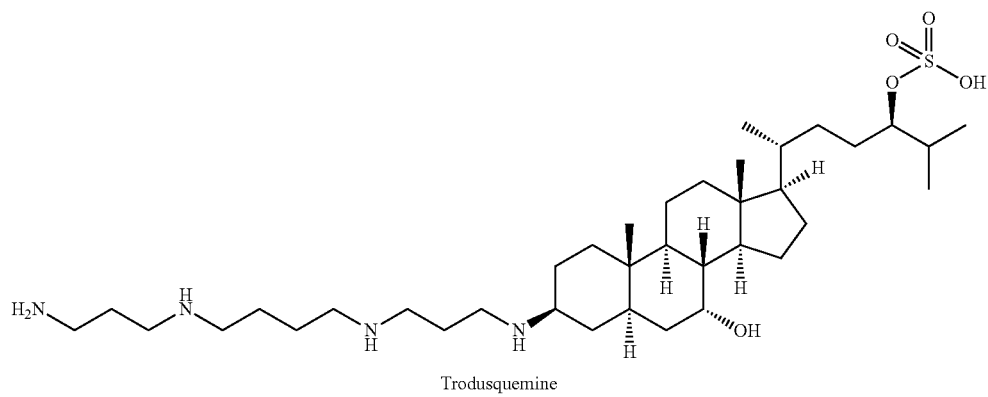
Trodusquemine
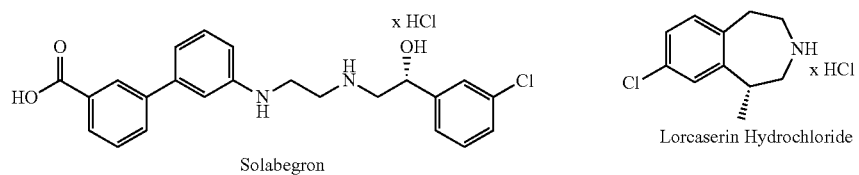
Solabegron
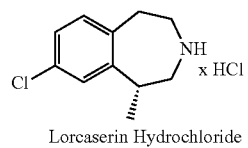
Lorcaserin Hydrochloride
L-152804
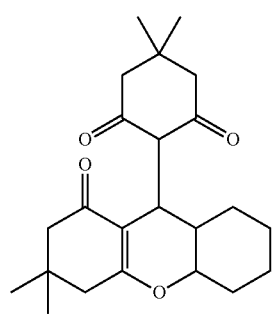
MB-06322
CS-917
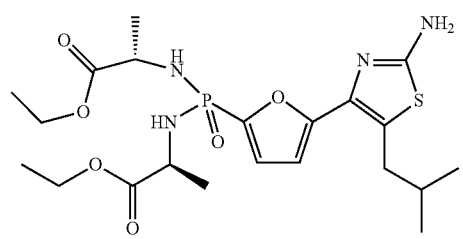
N5984
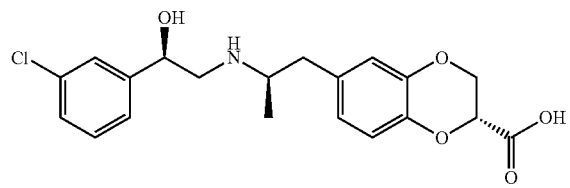
BIM-51077
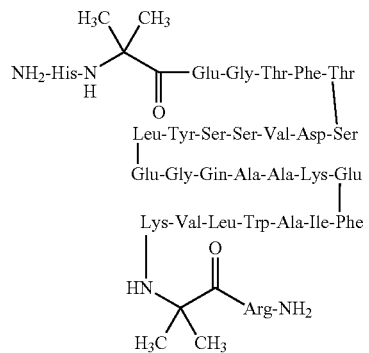

-continued
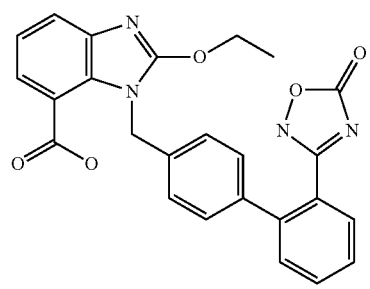
TAK-536
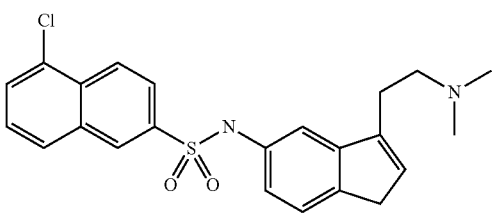
E-6837
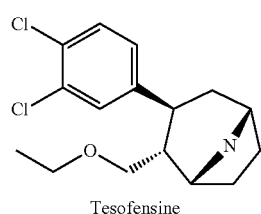
Tesofensine
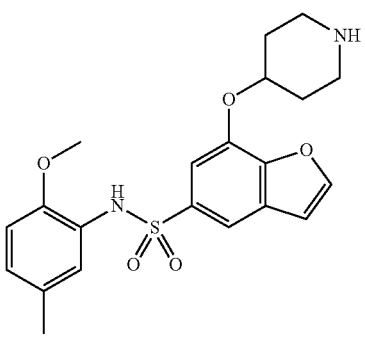
BVT-74316
ABT-341
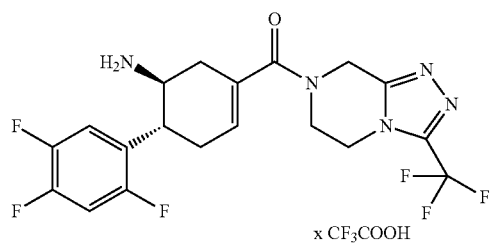
x CF₃COOH
MK-0364
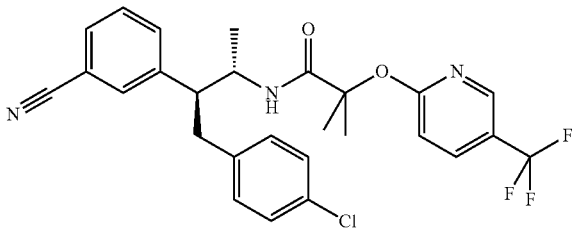
ABT-279
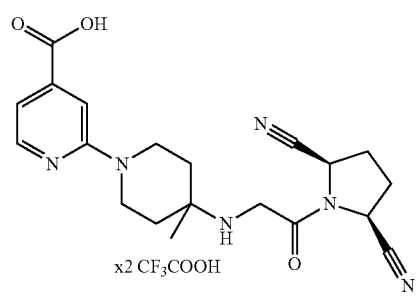
x2 CF₃COOH
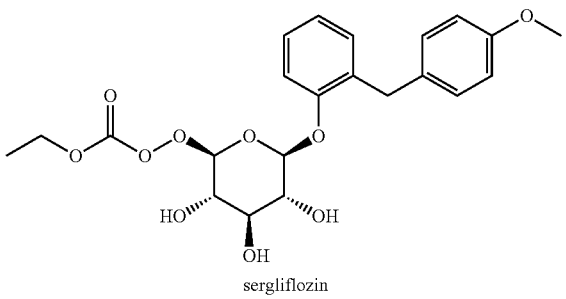
sergliflozin
SLV-319
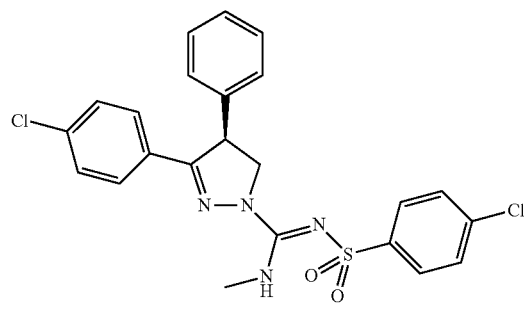
AVE 1625
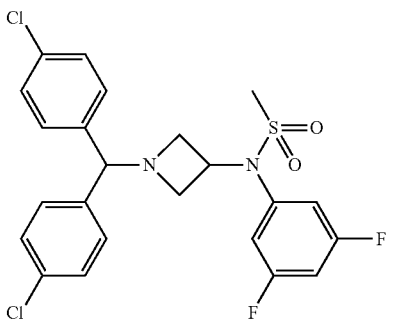

-continued
TAK-475
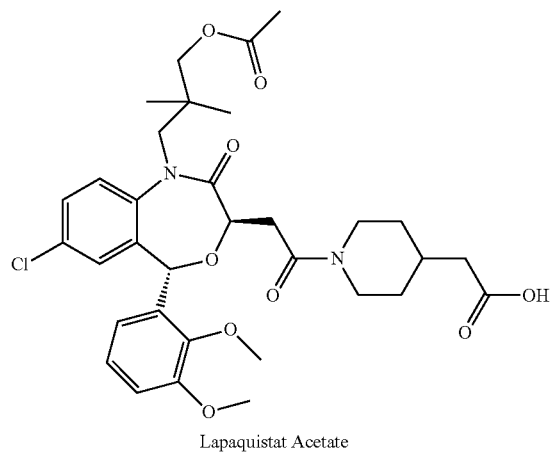
Lapaquistat Acetate
AS-1552133
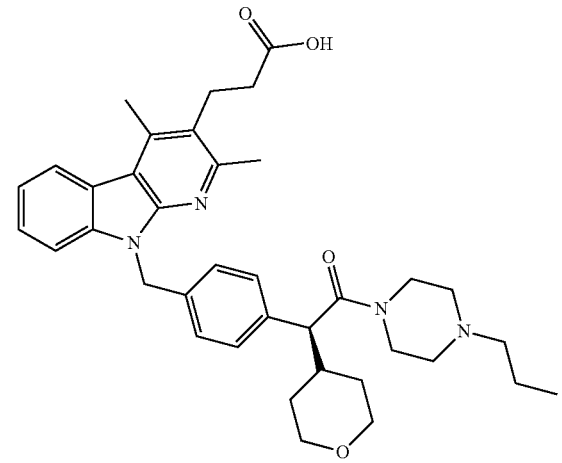
MB-07344
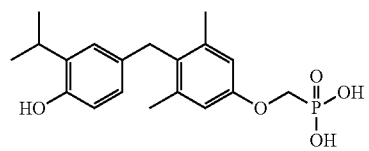
CKD-501
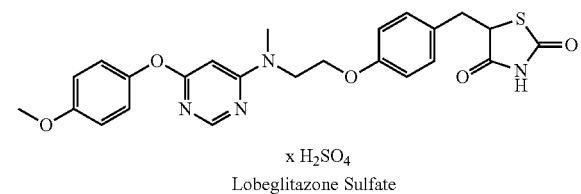
x H₂SO₄
Lobeglitazone Sulfate
MB-07811
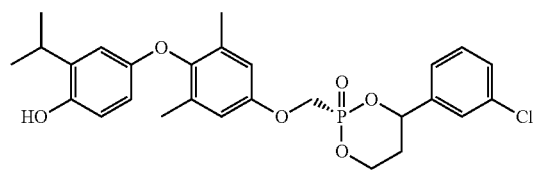
JMV-2959
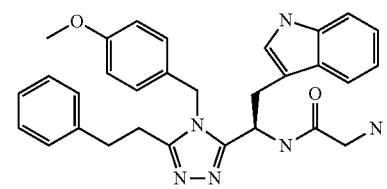
JMV-3002
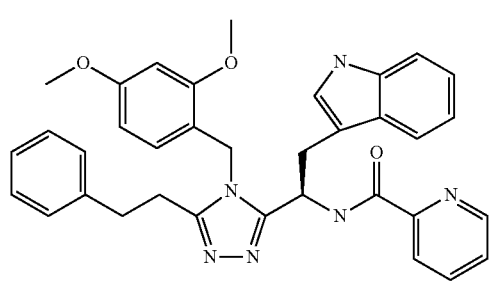
JMV-2810
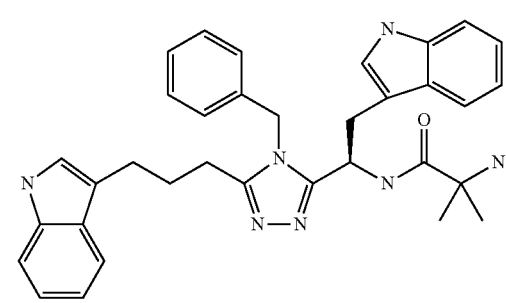
JMV-2951
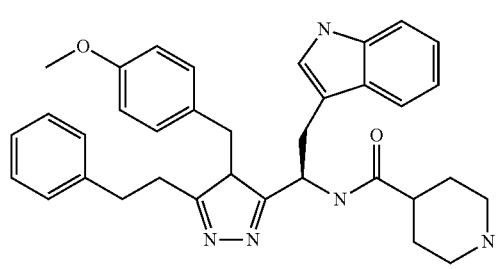
BMS-309403
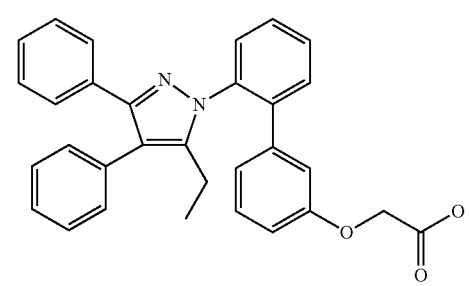

PSN-119-1
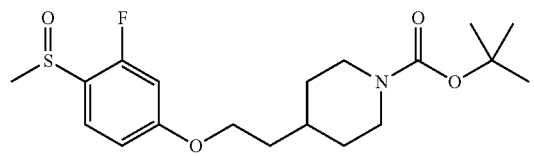
S-40755
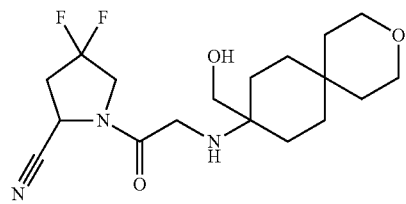
LY-2463665
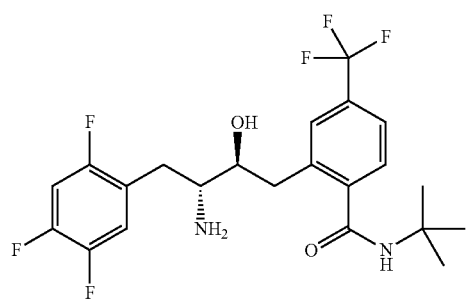
BMS-512148
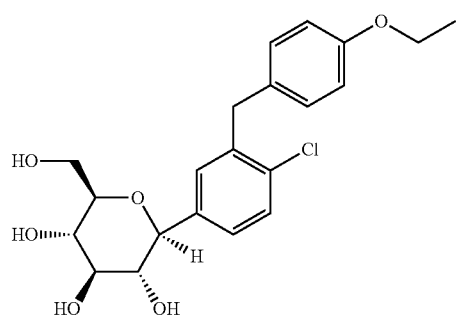
dapagliflozin
BI-1356
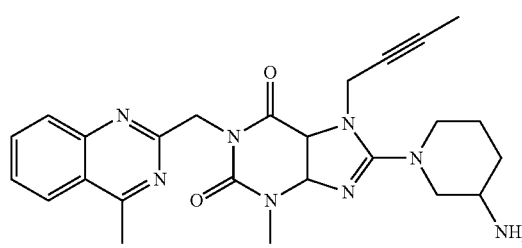
PT-429242
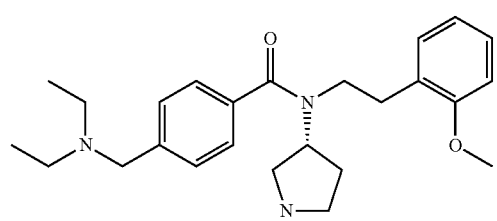
SLV-348
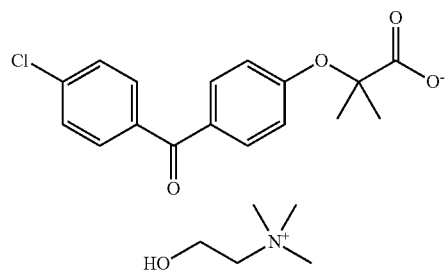
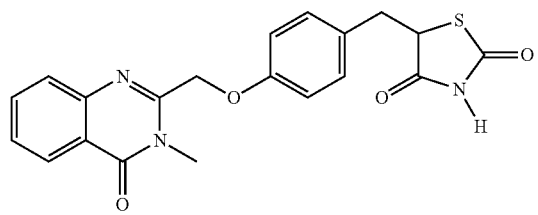
balaglotazpme
NPY-5-BY
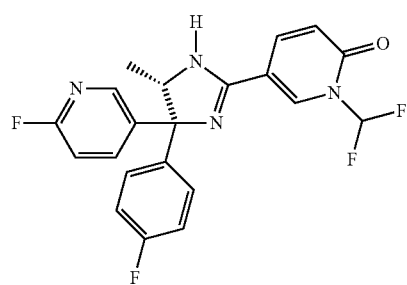
BMS-711939
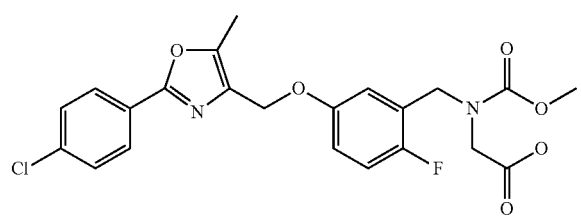
BMS-687453
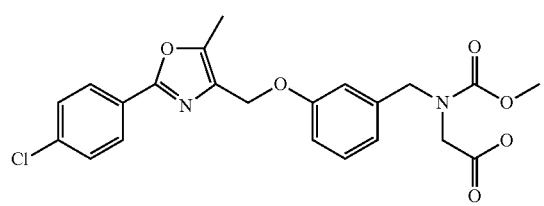
ST-3473
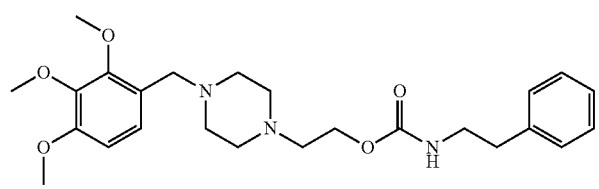

-continued
DOV-21947
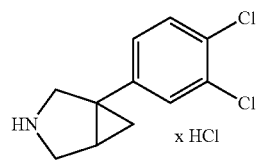
x HCl
DM-71
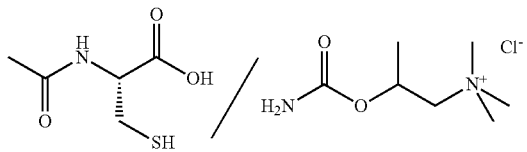
AEGR-733
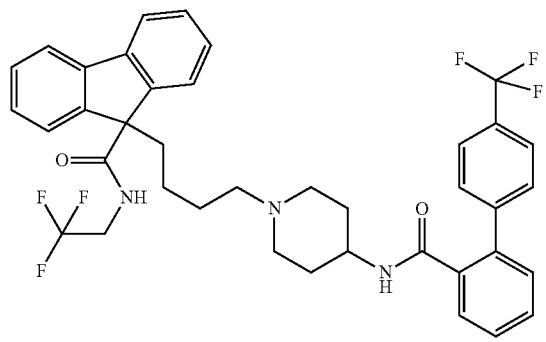
KY-382
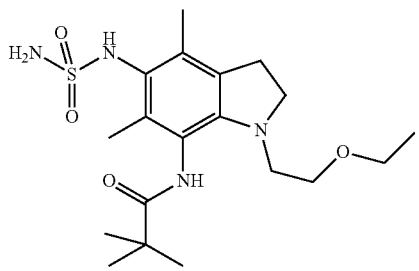
YIL-781
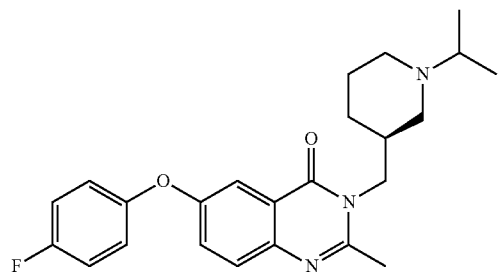
YIL-870
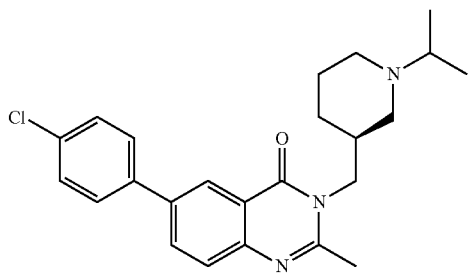
PRX-07034
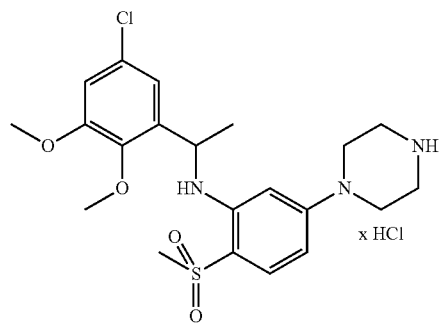
x HCl
PF-00389027
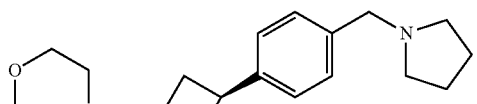

KB-3305

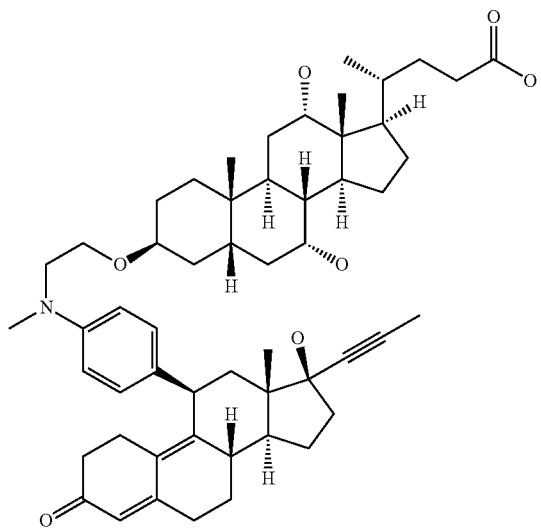

ISF-402

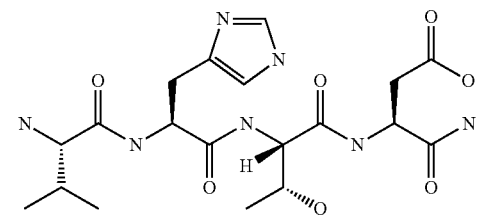

SRT-1720

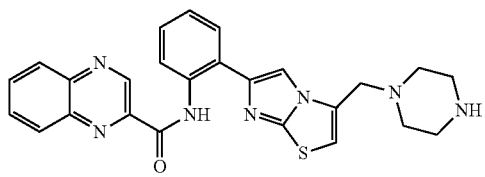

darapladib

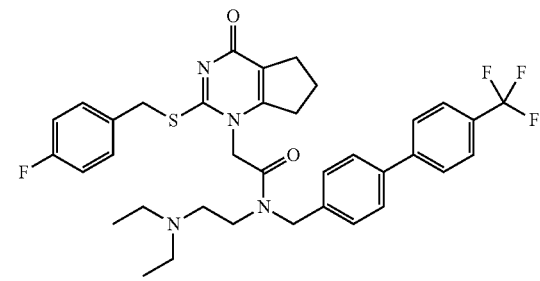

A-002

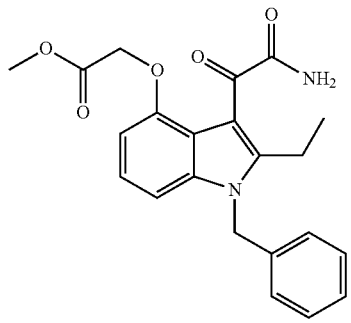

DITPA

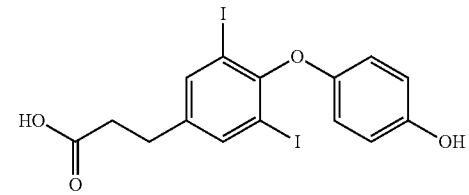

EXAMPLES

The examples and preparation methods adduced below serve to illustrate the invention, but without limiting it.

The inventive compounds of the formula I can be prepared with the aid of reactions known in principle. For example, the compounds were prepared according to the general reaction schemes which follow.

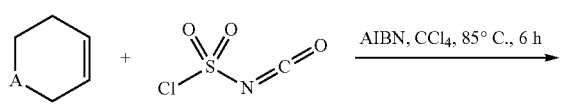

AIBN, CCl₄, 85° C., 6 h

-continued

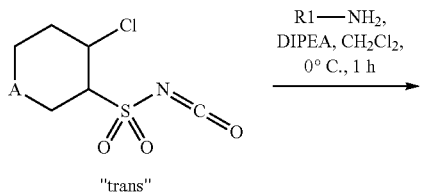

R1—NH₂,
DIPEA, CH₂Cl₂,
0° C., 1 h

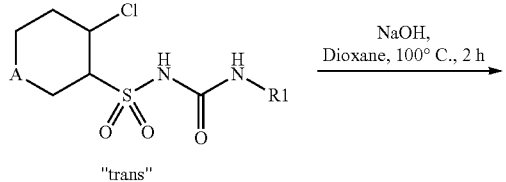

NaOH,
Dioxane, 100° C., 2 h

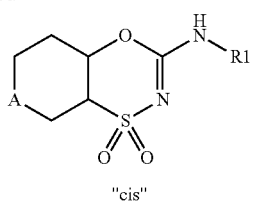

"cis"

A cyclic alkene can be used to prepare a corresponding chlorosulfonyl isocyanate in a free-radical reaction. This gives exclusively the cis configuration. Subsequently, reaction is effected with primary amines to give chlorosulfonylureas. The corresponding sodium salts cyclize when heated to give cis-4,4-dioxooxathiazines.

In the cases in which diastereomers or racemates form during the synthesis, these can be separated from one another by preparative HPLC.

Other inventive compounds can be obtained in other ways outlined by way of example in the scheme which follows.

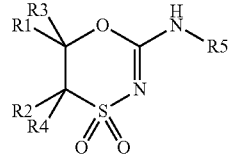

4-Tolylamide is reacted with thionyl chloride and pyridine to give N-sulfinyl-4-tolylamide. The latter reacts in a hetero-Diels-Alder reaction with an alkene to give 2-tolyl-4-oxathiazine. In the case of cyclic alkenes, exclusively the cis configuration is obtained. After oxidation to give 2-tolyl-4,4-dioxathiazine with 3-chloroperbenzoic acid, hydrolysis is effected with sodium hydroxide solution to give 1,2-dimethyl-2-hydroxycyclohexylsulfonamide. Further treatment with base and an isothiocyanate, and subsequent oxidative ring closure with NBS gives the desired 4,4-dioxooxathiazines.

In the cases in which diastereomers or racemates form during the synthesis, these can be separated from one another by preparative HPLC.

Other examples again were obtained as indicated in the following scheme:

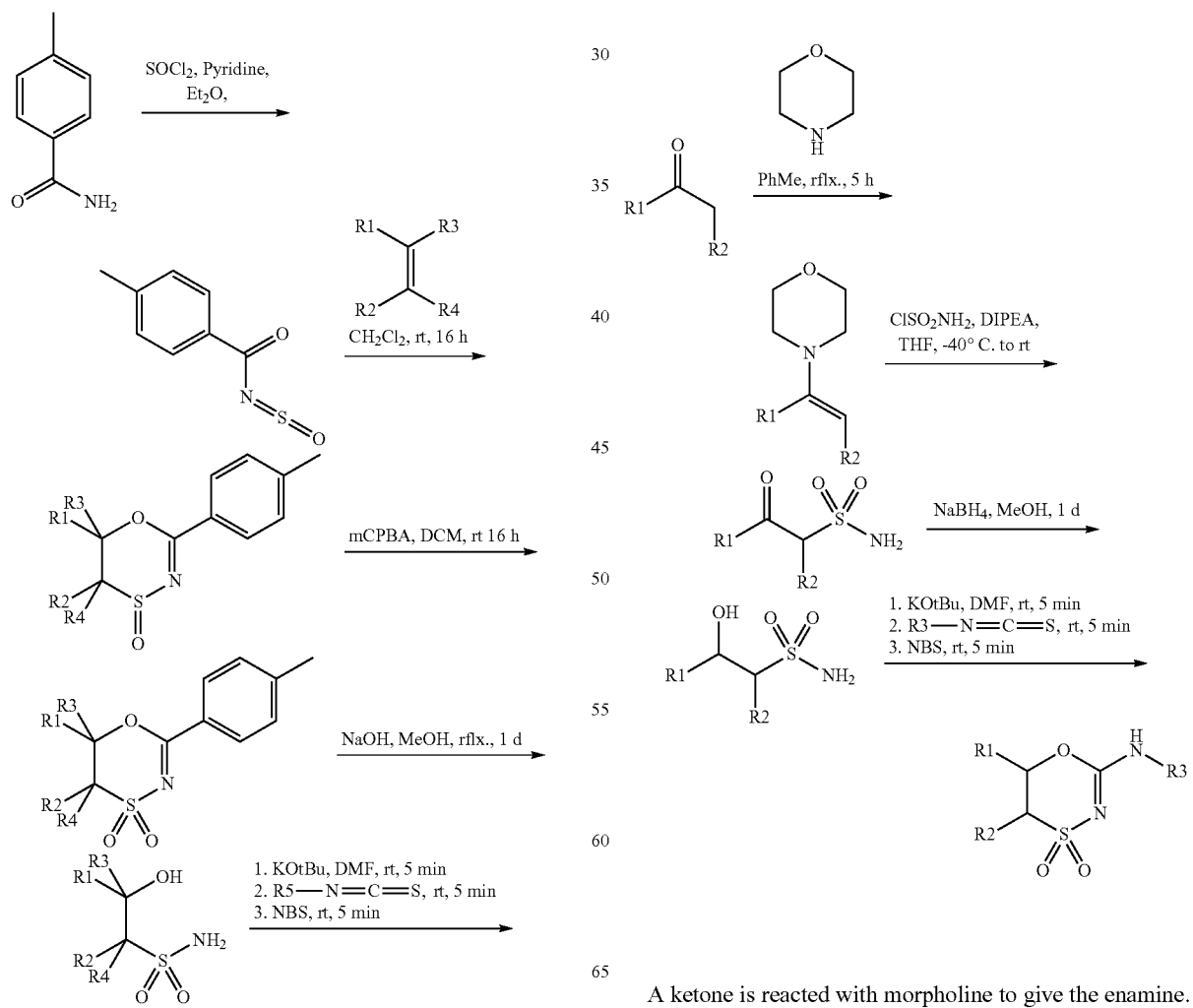

A ketone is reacted with morpholine to give the enamine. The latter is then treated with sulfamoyl chloride. The resulting ketosulfonamide can be reduced with a suitable reducing agent, for example sodium borohydride, to give the hydroxysulfonamide. This forms diastereomers and, in the case of cyclic ketones, cis/trans isomers, which can be separated from one another. The ratio of the diastereomers or cis/trans isomers depends on the nature of the R1 and R2 radicals and on the choice of reducing agent. The treatment of the hydroxysulfonamide with base and an isothiocyanate, and subsequent oxidative ring closure with NBS, gives the desired 4,4-dioxooxathiazines.

In the cases in which diastereomers or racemates form during the synthesis, these can be separated from one another by preparative HPLC.

Other examples again were obtained as indicated in the following scheme:

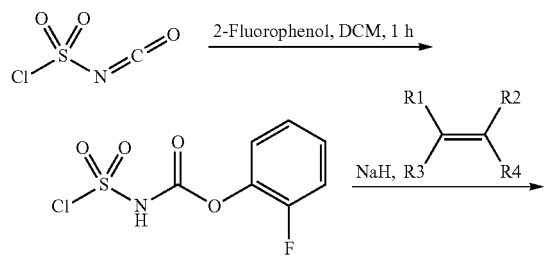

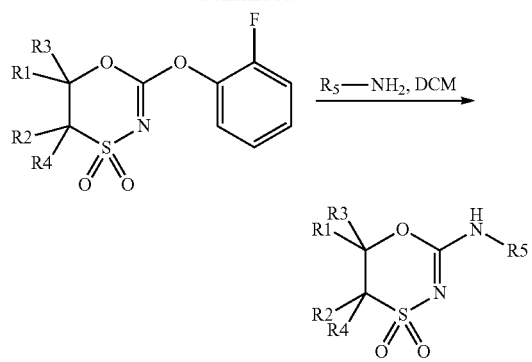

Chlorosulfonyl isocyanate is first reacted with 2-fluorophenol to give the corresponding chlorosulfonyl carbamate. The latter reacts in a 2+4 cycloaddition with an alkene to give the corresponding 2-(2-fluorophenoxy)-4,4-dioxothiazine. In the case of cyclic alkenes, exclusively the cis configuration is obtained. The reaction with amines affords the desired 4,4-dioxooxathiazines.

In the cases in which diastereomers or racemates form during the synthesis, these can be separated from one another by preparative HPLC.

Revise from here onwards and delete examples with $>C_8$.

| Example | CHEMISTRY | Method | Retention time | Molar mass (g/mol) | Name |
|---|---|---|---|---|---|
| 1 | | A | 1.244 | 286.4 | Cyclohexyl-(1,1-dioxo-4a,5,6,7,8,8a-hexahydro-1H-1lambda6-benzo[1,4,3]oxathiazin-3-yl)-amine |
| 2 | | C | 4.648 | 286.4 | (−)-Cyclohexyl-((4aR,8aS)-1,1-dioxo-4a,5,6,7,8,8a-hexahydro-1H-1lambda6-benzo[1,4,3]oxathiazin-3-yl)-amine * |
| 3 | | C | 6.145 | 286.4 | (+)-Cyclohexyl-((4aS,8aR)-1,1-dioxo-4a,5,6,7,8,8a-hexahydro-1H-1lambda6-benzo[1,4,3]oxathiazin-3-yl)-amine * |
| 5 | | B | 9.494 | 326.5 | ((4aR,8aS)-1,1-Dioxo-4a,5,6,7,8,8a-hexahydro-1H-1lambda6-benzo[1,4,3]oxathiazin-3-yl)-(4-methyl-bicyclo[2.2.2]oct-1-yl)-amine * |

-continued

| Example | CHEMISTRY | Method | Retention time | Molar mass (g/mol) | Name |
|---|---|---|---|---|---|
| 7 | | D | 9.283 | 331.4 | 3-((4aS,8aR)-1,1-Dioxo-4a,5,6,7,8,8a-hexahydro-1H-1lambda6-benzo[1,4,3]oxathiazin-3-ylamino)-N,N-diethyl-propionamide * |
| 8 | | B | 6.973 | 356.5 | (−)-(1R,2S,3R,4S)-3-(−1,1-Dioxo-4a,5,6,7,8,8a-hexahydro-1H-1lambda6-benzo[1,4,3]oxathiazin-3-ylamino)-1,7,7-trimethyl-bicyclo[2.2.1]heptan-2-ol * |
| 9 | | C | 5.81 | 340.5 | (−1,1-Dioxo-4a,5,6,7,8,8a-hexahydro-1H-1lambda6-benzo[1,4,3]oxathiazin-3-yl)-((1R,2R,4R)-1,7,7-trimethyl-bicyclo[2.2.1]hept-2-yl)-amine * |
| 10 | | C | 6.152 | 294.4 | (−)-Benzyl-(−1,1-dioxo-4a,5,6,7,8,8a-hexahydro-1H-1lambda6-benzo[1,4,3]oxathiazin-3-yl)-amine * |
| 11 | | D | 7.222 | 331.4 | 3-(−1,1-Dioxo-4a,5,6,7,8,8a-hexahydro-1H-1lambda6-benzo[1,4,3]oxathiazin-3-ylamino)-N,N-diethyl-propionamide * |
| 13 | | B | 6.461 | 326.5 | ((4aS,8aR)-1,1-Dioxo-4a,5,6,7,8,8a-hexahydro-1H-1lambda6-benzo[1,4,3]oxathiazin-3-yl)-(4-methyl-bicyclo[2.2.2]oct-1-yl)-amine * |
| 14 | | C | 4.337 | 340.5 | (−1,1-Dioxo-4a,5,6,7,8,8a-hexahydro-1H-1lambda6-benzo[1,4,3]oxathiazin-3-yl)-((1R,2R,4R)-1,7,7-trimethyl-bicyclo[2.2.1]hept-2-yl)-amine * |

-continued

| Example | CHEMISTRY | Method | Retention time | Molar mass (g/mol) | Name |
|---------|-----------|--------|----------------|---------------------|------|
| 15 | | B | 6.256 | 356.5 | (−)-(1R,2S,3R,4S)-3-(−1,1-Dioxo-4a,5,6,7,8,8a-hexahydro-1H-1lambda6-benzo[1,4,3]oxathiazin-3-ylamino)-1,7,7-trimethyl-bicyclo[2.2.1]heptan-2-ol * |
| 16 | | C | 9.237 | 294.4 | (+)-Benzyl-(−1,1-dioxo-4a,5,6,7,8,8a-hexahydro-1H-1lambda6-benzo[1,4,3]oxathiazin-3-yl)-amine * |
| 20 | | A | 1.472 | 314.4 | Cyclooctyl-(1,1-dioxo-4a,5,6,7,8,8a-hexahydro-1H-1lambda6-benzo[1,4,3]oxathiazin-3-yl)-amine |
| 21 | | A | 1.336 | 320.4 | (1,1-Dioxo-4a,5,6,7,8,8a-hexahydro-1H-1lambda6-benzo[1,4,3]oxathiazin-3-yl)-(R)-indan-1-yl-amine |
| 22 | | A | 1.477 | 314.4 | ((S)-1-Cyclohexyl-ethyl)-(1,1-dioxo-4a,5,6,7,8,8a-hexahydro-1H-1lambda6-benzo[1,4,3]oxathiazin-3-yl)-amine |
| 23 | | A | 1.58 | 328.5 | (1,1-Dioxo-4a,5,6,7,8,8a-hexahydro-1H-1lambda6-benzo[1,4,3]oxathiazin-3-yl)-(3,3,5-trimethyl-cyclohexyl)-amine |
| 24 | | A | 1.351 | 322.4 | (1,1-Dioxo-4a,5,6,7,8,8a-hexahydro-1H-1lambda6-benzo[1,4,3]oxathiazin-3-yl)-(1-methyl-1-phenyl-ethyl)amine |

-continued

| Example | CHEMISTRY | Method | Retention time | Molar mass (g/mol) | Name |
|---------|-----------|--------|----------------|--------------------|------|
| 25 | | A | 1.424 | 342.5 | (1,1-Dioxo-4a,5,6,7,8,8a-hexahydro-1H-1lambda6-benzo[1,4,3]oxathiazin-3-yl)-(2-methyl-1-thiophen-2-yl-propyl)-amine |
| 26 | | A | 1.177 | 272.4 | Cyclopentyl-(1,1-dioxo-4a,5,6,7,8,8a-hexahydro-1H-1lambda6-benzo[1,4,3]oxathiazin-3-yl)-amine |
| 27 | | A | 0.852 | 288.4 | (1,1-Dioxo-4a,5,6,7,8,8a-hexahydro-1H-1lambda6-benzo[1,4,3]oxathiazin-3-yl)-(tetrahydro-pyran-4-yl)-amine |
| 28 | | A | 1.357 | 300.4 | Cycloheptyl-(1,1-dioxo-4a,5,6,7,8,8a-hexahydro-1H-1lambda6-benzo[1,4,3]oxathiazin-3-yl)-amine |
| 29 | | A | 1.475 | 314.4 | ((R)-1-Cyclohexyl-ethyl)-(1,1-dioxo-4a,5,6,7,8,8a-hexahydro-1H-1lambda6-benzo[1,4,3]oxathiazin-3-yl)-amine |
| 31 | | A | 0.817 | 288.4 | (1R,2S)-2-(1,1-Dioxo-4a,5,6,7,8,8a-hexahydro-1H-1lambda6-benzo[1,4,3]oxathiazin-3-ylamino)-cyclopentanol |
| 35 | | A | 1.771 | 342.5 | (1,1-Dioxo-4a,5,6,7,8,8a-hexahydro-1H-1lambda6-benzo[1,4,3]oxathiazin-3-yl)-(3,3,5,5-tetramethyl-cyclohexyl)-amine |

-continued

| Example | CHEMISTRY | Method | Retention time | Molar mass (g/mol) | Name |
|---------|-----------|--------|----------------|--------------------|------|
| 36 | | A | 1.553 | 340.5 | (1,1-Dioxo-4a,5,6,7,8,8a-hexahydro-1H-1lambda6-benzo[1,4,3]oxathiazin-3-yl)-((1R,2S,4R)-1,7,7-trimethyl-bicyclo[2.2.1]hept-2-yl)-amine |
| 38 | | A | 1.289 | 356.5 | (1R,2S,3S,4S)-3-(1,1-Dioxo-4a,5,6,7,8,8a-hexahydro-1H-1lambda6-benzo[1,4,3]oxathiazin-3-ylamino)-1,7,7-trimethyl-bicyclo[2.2.1]heptan-2-ol |
| 39 | | A | 1.264 | 298.4 | Dicyclopropylmethyl-(1,1-dioxo-4a,5,6,7,8,8a-hexahydro-1H-1lambda6-benzo[1,4,3]oxathiazin-3-yl)-amine |
| 40 | | A | 0.786 | 343.5 | (1,1-Dioxo-4a,5,6,7,8,8a-hexahydro-1H-1lambda6-benzo[1,4,3]oxathiazin-3-yl)-(2,2,6,6-tetramethyl-piperidin-4-yl)-amine |
| 41 | | A | 1.144 | 342.5 | 3-(1,1-Dioxo-4a,5,6,7,8,8a-hexahydro-1H-1lambda6-benzo[1,4,3]oxathiazin-3-ylamino)-7,7-dimethyl-bicyclo[2.2.1]heptan-2-ol |

-continued

| Example | CHEMISTRY | Method | Retention time | Molar mass (g/mol) | Name |
|---|---|---|---|---|---|
| 42 | | A | 1.145 | 340.4 | 3-(1,1-Dioxo-4a,5,6,7,8,8a-hexahydro-1H-1lambda6-benzo[1,4,3]oxathiazin-3-ylamino)-7-cyclopropyl-bicyclo[2.2.1]heptan-2-ol |
| 43 | | A | 0.831 | 302.4 | 4-(1,1-Dioxo-4a,5,6,7,8,8a-hexahydro-1H-1lambda6-benzo[1,4,3]oxathiazin-3-ylamino)-cyclohexanol |
| 44 | | A | 1.034 | 316.4 | 1-[(1,1-Dioxo-4a,5,6,7,8,8a-hexahydro-1H-1lambda6-benzo[1,4,3]oxathiazin-3-ylamino)-methyl]-cyclohexanol |
| 45 | | A | 0.916 | 341.4 | (1R,2R,3S,4S)-3-(−1,1-Dioxo-4a,5,6,7,8,8a-hexahydro-1H-1lambda6-benzo[1,4,3]oxathiazin-3-ylamino)-bicyclo[2.2.1]heptane-2-carboxylic acid amide |
| 46 | | A | 0.98 | 341.4 | (1R,2R,3S,4S)-3-(−1,1-Dioxo-4a,5,6,7,8,8a-hexahydro-1H-1lambda6-benzo[1,4,3]oxathiazin-3-ylamino)-bicyclo[2.2.1]heptane-2-carboxylic acid amide |
| 47 | | A | 1.043 | 302.4 | (1,1-Dioxo-4a,5,6,7,8,8a-hexahydro-1H-1lambda6-benzo[1,4,3]oxathiazin-3-yl)-(tetrahydro-pyran-2-ylmethyl)-amine |
| 48 | | A | 1.343 | 352.5 | (1,1-Dioxo-4a,5,6,7,8,8a-hexahydro-1H-1lambda6-benzo[1,4,3]oxathiazin-3-yl)-thiochroman-4-yl-amine |

-continued

| Example | CHEMISTRY | Method | Retention time | Molar mass (g/mol) | Name |
|---|---|---|---|---|---|
| 49 | | A | 0.903 | 316.4 | [2-(1,1-Dioxo-4a,5,6,7,8,8a-hexahydro-1H-1lambda6-benzo[1,4,3]oxathiazin-3-ylamino)-2-methyl-cyclopentyl]-methanol |
| 50 | | M | 11.255 | 300.4 | Cycloheptyl-((4aS,8aR)-1,1-dioxo-4a,5,6,7,8,8a-hexahydro-1H-1lambda6-benzo[1,4,3]oxathiazin-3-yl)-amine |
| 51 | | M | 14.565 | 300.4 | Cycloheptyl-((4aR,8aS)-1,1-dioxo-4a,5,6,7,8,8a-hexahydro-1H-1lambda6-benzo[1,4,3]oxathiazin-3-yl)-amine |
| 53 | | A | 1.615 | 340.5 | (1,1-Dioxo-4a,5,6,7,8,8a-hexahydro-1H-1lambda6-benzo[1,4,3]oxathiazin-3-yl)-((1S,4R,5R)-1-isopropyl-4-methyl-bicyclo[3.1.0]hex-3-yl)-amine |
| 54 | | A | 1.398 | 312.4 | (1R,5R)-Bicyclo[3.2.1]oct-2-yl-(1,1-dioxo-4a,5,6,7,8,8a-hexahydro-1H-1lambda6-benzo[1,4,3]oxathiazin-3-yl)-amine |
| 55 | | A | 1.66 | 330.5 | (1,1-Dioxo-4a,5,6,7,8,8a-hexahydro-1H-1lambda6-benzo[1,4,3]oxathiazin-3-yl)-(1-isobutyl-3-methyl-butyl)-amine |
| 56 | | A | 1.603 | 340.5 | (1,1-Dioxo-4a,5,6,7,8,8a-hexahydro-1H-1lambda6-benzo[1,4,3]oxathiazin-3-yl)-((1S,2S,3S,5R)-2,6,6-trimethyl-bicyclo[3.1.1]hept-3-yl)-amine |
| 57 | | A | 1.217 | 322.4 | (4,4-Difluoro-cyclohexyl)-(1,1-dioxo-4a,5,6,7,8,8a-hexahydro-1H-1lambda6-benzo[1,4,3]oxathiazin-3-yl)-amine |

-continued

| Example | CHEMISTRY | Method | Retention time | Molar mass (g/mol) | Name |
|---|---|---|---|---|---|
| 58 | | A | 1.958 | 382.6 | ((4aS,8aR)-1,1-Dioxo-4a,5,6,7,8,8a-hexahydro-1H-1lambda6-benzo[1,4,3]oxathiazin-3-yl)-(4-pentyl-bicyclo[2.2.2]oct-1-yl)-amine |
| 59 | | A | 1.01 | 316.4 | [(1R,2R)-2-((4aS,8aR)-1,1-Dioxo-4a,5,6,7,8,8a-hexahydro-1H-1lambda6-benzo[1,4,3]oxathiazin-3-ylamino)-cyclohexyl]-methanol |
| 61 | | A | 1.472 | 314.5 | (4,4-Dimethyl-cyclohexyl)-(1,1-dioxo-4a,5,6,7,8,8a-hexahydro-1H-1lambda6-benzo[1,4,3]oxathiazin-3-yl)-amine |
| 62 | | A | 1.297 | 298.4 | (1R,2R,4S)-Bicyclo[2.2.1]hept-2-yl-((5S,6R)-1,1-dioxo-4a,5,6,7,8,8a-hexahydro-1H-1lambda6-benzo[1,4,3]oxathiazin-3-yl)-amine |
| 64 | | A | 1.391 | 312.4 | (1,1-Dioxo-1,4a,5,6,7,7a-hexahydro-1lambda6-cyclopenta[1,4,3]oxathiazin-3-yl)-(4-methyl-bicyclo[2.2.2]oct-1-yl)-amine |
| 65 | | A | 1.1 | 313.4 | (1,1-Dioxo-4a,5,6,7,8,8a-hexahydro-1H-1lambda6-benzo[1,4,3]oxathiazin-3-yl)-(hexahydro-cyclopenta[c]pyrrol-2-yl)-amine |
| 66 | | A | 1.021 | 301.4 | Azepan-1-yl-(1,1-dioxo-4a,5,6,7,8,8a-hexahydro-1H-1lambda6-benzo[1,4,3]oxathiazin-3-yl)-amine |

-continued

| Example | CHEMISTRY | Method | Retention time | Molar mass (g/mol) | Name |
|---|---|---|---|---|---|
| 67 | | A | 1.071 | 315.4 | (2,6-Dimethyl-piperidin-1-yl)-(1,1-dioxo-4a,5,6,7,8,8a-hexahydro-1H-1lambda6-benzo[1,4,3]oxathiazin-3-yl)-amine |
| 68 | | A | 1.213 | 330.4 | (1,1-Dioxo-4a,5,6,7,8,8a-hexahydro-1H-1lambda6-benzo[1,4,3]oxathiazin-3-yl)-(4-fluoro-bicyclo[2.2.2]oct-1-yl)-amine |
| 71 | | A | 1.241 | 315.4 | N-Cyclohexyl-N'-(1,1-dioxo-4a,5,6,7,8,8a-hexahydro-1H-1lambda6-benzo[1,4,3]oxathiazin-3-yl)-N-methyl-hydrazine |
| 72 | | A | 1.202 | 298.4 | Bicyclo[2.2.2]oct-1-yl-(1,1-dioxo-1,4a,5,6,7,7a-hexahydro-1lambda6-cyclopenta[1,4,3]oxathiazin-3-yl)-amine |
| 73 | | B | 5.707 | 330.4 | ((4aS,8aR)-1,1-Dioxo-4a,5,6,7,8,8a-hexahydro-1H-1lambda6-benzo[1,4,3]oxathiazin-3-yl)-(4-fluoro-bicyclo[2.2.2]oct-1-yl)-amine * |
| 74 | | B | 7.45 | 330.4 | ((4aR,8aS)-1,1-Dioxo-4a,5,6,7,8,8a-hexahydro-1H-1lambda6-benzo[1,4,3]oxathiazin-3-yl)-(4-fluoro-bicyclo[2.2.2]oct-1-yl)-amine * |
| 75 | | F | 24.152 | 312.4 | (+)-Bicyclo[2.2.2]oct-1-yl-(−1,1-dioxo-4a,5,6,7,8,8a-hexahydro-1H-1lambda6-benzo[1,4,3]oxathiazin-3-yl)-amine * |
| 76 | | A | 0.882 | 328.4 | 4-(1,1-Dioxo-4a,5,6,7,8,8a-hexahydro-1H-1lambda6-benzo[1,4,3]oxathiazin-3-ylamino)-bicyclo[2.2.2]octan-1-ol |

-continued

| Example | CHEMISTRY | Method | Retention time | Molar mass (g/mol) | Name |
|---|---|---|---|---|---|
| 77 | | L | 0.717 | 341.5 | (−1,1-Dioxo-4a,5,6,7,8,8a-hexahydro-1H-1lambda6-benzo[1,4,3]oxathiazin-3-yl)-((1S,3R,5R)-9-methyl-9-aza-bicyclo[3.3.1]non-3-yl)-amine |
| 78 | | A | 1.587 | 346.4 | (2,3,4,5,6,7,8,9,10,11-Decabora-bicyclo[8.1.1]dodec-1-yl)-(1,1-dioxo-4a,5,6,7,8,8a-hexahydro-1H-1lambda6-benzo[1,4,3]oxathiazin-3-yl)-amine |
| 79 | | A | 1.383 | 300.4 | (1,1-Dioxo-4a,5,6,7,8,8a-hexahydro-1H-1lambda6-benzo[1,4,3]oxathiazin-3-yl)-(1-isopropyl-2-methyl-propyl)-amine |
| 80 | | A | 1.37 | 300.4 | Cyclohexylmethyl-(1,1-dioxo-4a,5,6,7,8,8a-hexahydro-1H-1lambda6-benzo[1,4,3]oxathiazin-3-yl)-amine |
| 81 | | A | 0.789 | 302.4 | 4-(1,1-Dioxo-4a,5,6,7,8,8a-hexahydro-1H-1lambda6-benzo[1,4,3]oxathiazin-3-ylamino)-cyclohexanol |
| 82 | | F | 15.169 | 312.4 | (−)-Bicyclo[2.2.2]oct-1-yl-(−1,1-dioxo-4a,5,6,7,8,8a-hexahydro-1H-1lambda6-benzo[1,4,3]oxathiazin-3-yl)-amine * |
| 83 | | A | 1.354 | 314.4 | Cyclohexyl-(4a,8a-dimethyl-1,1-dioxo-4a,5,6,7,8,8a-hexahydro-1H-1lambda6-benzo[1,4,3]oxathiazin-3-yl)-amine |
| 84 | | N | 0.689 | 288.4 | Cyclohexyl-(−1,1-dioxo-5,6,8,8a-tetrahydro-1H,4aH-4,7-dioxa-1lambda6-thia-2-aza-naphthalen-3-yl)-amine ** |

-continued

| Example | CHEMISTRY | Method | Retention time | Molar mass (g/mol) | Name |
|---|---|---|---|---|---|
| 85 | | N | 0.703 | 288.4 | Cyclohexyl-(−1,1-dioxo-5,6,8,8a-tetrahydro-1H,4aH-4,7-dioxa-1lambda6-thia-2-aza-naphthalen-3-yl)-amine |
| 86 | | P | 39.602 | 286.4 | Cyclohexyl-(−1,1-dioxo-4a,5,6,7,8,8a-hexahydro-1H-1lambda6-benzo[1,4,3]oxathiazin-3-yl)-amine *, ** |
| 87 | | P | 44.273 | 286.4 | Cyclohexyl-(−1,1-dioxo-4a,5,6,7,8,8a-hexahydro-1H-1lambda6-benzo[1,4,3]oxathiazin-3-yl)-amine *, ** |
| 88 | | N | 0.849 | 322.4 | Cyclohexyl-(7,7-difluoro-1,1-dioxo-4a,5,6,7,8,8a-hexahydro-1H-1lambda6-benzo[1,4,3]oxathiazin-3-yl)-amine |
| 89 | | L | 1.005 | 300.4 | Cyclohexyl-(−4a-methyl-1,1-dioxo-4a,5,6,7,8,8a-hexahydro-1H-1lambda6-benzo[1,4,3]oxathiazin-3-yl)-amine |

* isomerically pure compound
** trans

Chromatography methods:

Method A
Column: YMC J'spere ODS H80, 80 Å, S-4 µm, 20 × 2.1 mm
Eluent: 0 min 90% H$_2$O (0.05% TFA) – 1.9 min 95% acetonitrile – 2.4 min 95% acetonitrile – 2.45 min 10% acetonitrile (30° C., flow rate 1 ml/min)

Method B
Column: Chiralpak AS-H/75, 5 µm, 250 × 4.6 mm
Eluent: heptane:ethanol:methanol 5:1:1 (30° C., flow rate 1 ml/min)

Method C
Column: Chiralpak AD-H/44, 5 µm, 250 × 4.6 mm
Eluent: heptane:ethanol:methanol 5:1:1 (30° C., flow rate 1ml/min)

Method D
Column: Chiralpak AD-H/39, 5 µm, 250 × 4.6 mm
Eluent: heptane:ethanol:methanol 5:1:1 (30° C., flow rate 1 ml/min)

Method E
Column: Chiralpak AS-H/52, 5 µm, 250 × 4.6 mm
Eluent: heptane:ethanol:methanol 5:1:1 (30° C., flow rate 1 ml/min)

Method F
Column: Chiralpak AS-H/52, 5 µm, 250 × 4.6 mm
Eluent: heptane:ethanol:methanol 10:1:1 (30° C., flow rate 1 ml/min)

Method K
Column: YMC J'spere 33 × 2 mm 4 µM
Eluent: 0 min 95% H$_2$O (0.05% TFA) – 0.5 min 95% acetonitrile (0.05% TFA) – 3.5 min 95% acetonitrile – 4.0 min 95% acetonitrile (30° C., flow rate 1 ml/min)

Method L
Column: YMC J'spere ODS H80, 80 Å, S-4 µm, 20 × 2.1 mm
Eluent: 0 min 96% H$_2$O (0.05% TFA) – 2.0 min 95% acetonitrile – 2.4 min 95% acetonitrile – 2.45 min 4% acetonitrile (30° C., flow rate 1 ml/min)

Method M
Column: Chiralpak AS-H/52, 5 µm, 250 × 4.6 mm
Eluent: heptane:ethanol:methanol 10:1:1, preconditioned with TFA (30° C., flow rate 1 ml/min)

Method N
Column: Mercury MS, Luna C18(2), S-3 µm, 10 × 2.0 mm

| Example | CHEMISTRY | Method | Retention time | Molar mass (g/mol) | Name |
|---|---|---|---|---|---|

Eluent: 0 min 93% H$_2$O (0.05% TFA) – 1.2 min 95% acetonitrile – 1.4 min 95% acetonitrile – 1.45 min 7% acetonitrile (30° C., flow rate 1.1 ml/min)
Method O
Column: Mercury MS, Luna C18(2), S-3 µm, 10 × 2.0 mm
Eluent: 0 min 93% H$_2$O (0.05% TFA) – 1.0 min 95% acetonitrile – 1.45 min 95% acetonitrile – 1.5 min 7% acetonitrile (30° C., flow rate 1.1 ml/min)
Method P
Column: Chiralpak IA/103
Eluent: heptane:ethanol:methanol 40:1:1 + 0.1% trifluoroacetic acid (30° C., flow rate 1 ml/min)

The efficacy of the compounds was tested as follows:
Enzymatic 11beta-HSD1 test:

To measure the activity of the compounds, an SPA-based detection method (Solly et al. 2005) was employed. First of all, 20 µl of the human 11β-HSD1 microsome fraction (0.2 µg of protein), prepared in 50 mM HEPES, 0.1% BSA (w/v), were applied to a plate with 384 wells. The test compounds (0.09 µl) were applied to the assay plate in 100% DMSO. The reaction was started by addition of 20 µl of [1,2-$^3$H]-cortisone (0.1 µCi/100 mM) in assay buffer comprising 25 mM HEPES, 100 mM KCl, 5 mM NaCl, 2 mM MgCl$_2$ and 0.25 mM NADPH. The plate was agitated at 37° C. for 1 hour. At the same time, a stop solution comprising 20 mg/ml SPA-PVT beads, 1.6 mg/ml monoclonal cortisol antibody and 0.01 mM SSR110887 (inhibitor from the Biovitrium patent) in 50 mM HEPES, 1 M NaCl and 1 M KCl was stirred at room temperature. To stop the reaction, 25 µl of the stop solution were added to each well. The plate was agitated gently at room temperature for 1 further hour and then centrifuged at 500 g$_{av}$ for 1 mM, in order that the SPA beads could settle out. The plate was then read in a Wallac-1450-Microbeta unit with a standard SPA program (counting time 1 min/well). The comparative compound was glycyrrhetinic acid.

Protein and radioactive substrate were dispensed with a Biomek FX unit (Beckman Coulter) for handling liquids. The test compounds were added with a Cybi-Well equipped with a 90 nl pin tool (CyBio).

Lit.: Solly S, Mundt S S, Zokian H J, Juy-Fang Ding G, Hermanowski-Vosatka A, Strulovici B and Zheng W. High-throughput screening of 11β-Hydroxysteroid dehydrogenase type 1 in scintillation proximity format. Assay Drug Dev Technol 2005; 3:377-384.

TABLE 2

Biological activity in nanomolar (nM)

| Example | IC$_{50}$ (nM) |
|---|---|
| 1 | 31 |
| 2 | 575 |
| 3 | 24 |
| 5 | 8 |
| 9 | 5 |
| 10 | 104 |
| 13 | 5 |
| 14 | 236 |
| 20 | 13 |
| 23 | 20 |
| 24 | 215 |
| 25 | 121 |
| 26 | 425 |
| 27 | 671 |
| 28 | 22 |
| 29 | 275 |
| 35 | 11 |
| 36 | 59 |
| 38 | 570 |
| 39 | 440 |
| 41 | 497 |
| 47 | 165 |
| 48 | 93 |
| 50 | 24 |
| 51 | 300 |
| 53 | 54 |
| 54 | 29 |
| 55 | 670 |
| 56 | 16 |
| 57 | 405 |
| 59 | 658 |
| 61 | 64 |
| 62 | 43 |
| 64 | 38 |
| 65 | 308 |
| 66 | 148 |
| 68 | 23 |
| 72 | 74 |
| 73 | 13 |
| 74 | 18 |
| 75 | 11 |
| 76 | 49 |
| 78 | 2 |
| 80 | 98 |
| 81 | 355 |
| 82 | 9 |
| 83 | 18 |
| 84 | 779 |
| 86 | 655 |
| 87 | 197 |
| 88 | 234 |
| 89 | 49 |

It can be inferred from the test data that the compounds of the formula I inhibit 11beta-HSD1 (11beta-hydroxysteroid dehydrogenase type 1), and are thus of good suitability for treatment of hyperglycemia, insulin resistance, diabetes, obesity, lipid metabolism disorders, high blood pressure, cognitive improvement, elevated intraocular pressure, promotion of wound healing, and other diseases.

The preparation of some examples is described in detail hereinafter; the remaining compounds of the formula I were obtained analogously:

Experimental

Cyclohexyl-(1,1-dioxo-4-a,5,6,7,8,8a-hexahydro-1H-1lambda6-benzo[1,4,3]oxathiazin-3-yl)amine

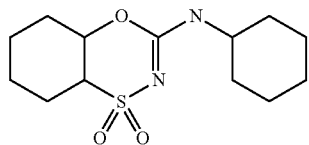 [SMILES: O=S1(=O)N=C(NC2CCCCC2)OC2CCCCC21]

Under inert gas, 10 mmol of cyclohexylamine and 50 mmol of diisopropylethylamine were initially charged in 5 ml of dichloromethane and then, while cooling with ice, 10 mmol of 2-chlorocyclohexanesulfonyl isocyanate dissolved in 5 ml of dichloromethane were added dropwise and the mixture was stirred for 1 hour. The completeness of the conversion was checked by LCMS. If cyclohexylamine was still present, another 0.4 eq of 2-chlorocyclohexanesulfonyl isocyanate was added and the mixture was allowed to come to room temperature while stirring overnight. The reaction solution was diluted with 50 ml of dichloromethane and extracted twice with 20 ml of 10% $KHSO_4$ solution, and the organic phase was dried over $MgSO_4$ and concentrated by rotary evaporation (3.08 g). The residue was then admixed with 0.5 eq (based on the amine) of 0.1 N NaOH. Addition of dioxane (for example in the case of 20 ml of 0.1 N NaOH/5 ml of dioxane) and heated to 100° C. At 100° C., a clear solution is formed. If some starting material is still present, 1-2 drops of 1 N NaOH were added. After a further 30 minutes at 100° C., full conversion. After cooling, 30 ml of dichloromethane were added and the mixture was washed twice with 10 ml of saturated $Na_2CO_3$ solution. The aqueous solution was extracted once more with 20 ml of dichloromethane. The combined organic phases were dried over $MgSO_4$ and concentrated by rotary evaporation. The residue was dissolved in DMF and purified in a purification laboratory by means of preparative HPLC. This gave the product (244 mg) with a molecular weight of 286.4 g/mol ($C_{13}H_{22}N_2O_3S$); MS (ESI): m/e=287 (M+H+).

Compounds 1-82 were synthesized by this preparation method:

(−)-Cyclohexyl-((4aR,8aS)-1,1-dioxo-4-a,5,6,7,8,8a-hexahydro-1H-1lambda6-benzo[1,4,3]oxathiazin-3-yl)amine*

(+)-Cyclohexyl-((4aS,8aR)-1,1-dioxo-4-a,5,6,7,8,8a-hexahydro-1H-1lambda6-benzo[1,4,3]oxathiazin-3-yl)amine*

((4aR,8aS)-1,1-Dioxo-4-a,5,6,7,8,8a-hexahydro-1H-1lambda6-benzo[1,4,3]oxathiazin-3-yl)-(4-methylbicyclo[2.2.2]oct-1-yl)amine*

3-((4aS,8aR)-1,1-Dioxo-4-a,5,6,7,8,8a-hexahydro-1H-1lambda6-benzo[1,4,3]oxathiazin-3-ylamino)-N,N-diethylpropionamide*

(−)-(1R,2S,3R,4S)-3-(1,1-Dioxo-4-a,5,6,7,8,8a-hexahydro-1H-1lambda6-benzo[1,4,3]oxathiazin-3-ylamino)-1,7,7-trimethylbicyclo[2.2.1]heptan-2-ol*

(1,1-Dioxo-4-a,5,6,7,8,8a-hexahydro-1H-1lambda6-benzo[1,4,3]oxathiazin-3-yl)-((1R,2R,4R)-1,7,7-trimethylbicyclo[2.2.1]hept-2-yl)amine*

(−)-Benzyl-(1,1-dioxo-4-a,5,6,7,8,8a-hexahydro-1H-1lambda6-benzo[1,4,3]oxathiazin-3-yl)amine*

3-(1,1-Dioxo-4a,5,6,7,8,8a-hexahydro-1H-1lambda6-benzo[1,4,3]oxathiazin-3-ylamino)-N,N-diethylpropionamide*

((4aS,8aR)-1,1-Dioxo-4-a,5,6,7,8,8a-hexahydro-1H-1lambda6-benzo[1,4,3]oxathiazin-3-yl)-(4-methylbicyclo[2.2.2]oct-1-yl)amine*

(1,1-Dioxo-4-a,5,6,7,8,8a-hexahydro-1H-1lambda6-benzo[1,4,3]oxathiazin-3-yl)-((1R,2R,4R)-1,7,7-trimethylbicyclo[2.2.1]hept-2-yl)amine*

(−)-(1R,2S,3R,4S)-3-(1,1-Dioxo-4-a,5,6,7,8,8a-hexahydro-1H-1lambda6-benzo[1,4,3]oxathiazin-3-ylamino)-1,7,7-trimethylbicyclo[2.2.1]heptan-2-ol*

(+)-Benzyl-(1,1-dioxo-4-a,5,6,7,8,8a-hexahydro-1H-1lambda6-benzo[1,4,3]oxathiazin-3-yl)amine*

(1,1-Dioxo-4-a,5,6,7,8,8a-hexahydro-1H-1lambda6-benzo[1,4,3]oxathiazin-3-yl)-(hexahydro-2,5-methanopentalen-3a-yl)amine Cyclooctyl-(1,1-dioxo-4-a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-(R)-indan-1-ylamine ((S)-1-Cyclohexylethyl)-(1,1-dioxo-4-a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-(3,3,5-trimethylcyclohexyl)amine (1,1-Dioxo-4-a,5,6,7,8,8a-hexahydro-1H-1lambda6-benzo[1,4,3]oxathiazin-3-yl)-(1-methyl-1-phenylethyl)amine (1,1-Dioxo-4-a,5,6,7,8,8a-hexahydro-1H-1lambda6-benzo[1,4,3]oxathiazin-3-yl)-(2-methyl-1-thiophen-2-ylpropyl)amine Cyclopentyl-(1,1-dioxo-4-a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-(tetrahydropyran-4-yl)amine Cycloheptyl-(1,1-dioxo-4-a,5,6,7,8,8a-hexahydro-1H-1lambda6-benzo[1,4,3]oxathiazin-3-yl)amine ((R)-1-Cyclohexylethyl)-(1,1-dioxo-4-a,5,6,7,8,8a-hexahydro-1H-1lambda6-benzo[1,4,3]oxathiazin-3-yl)amine (1R,2S)-2-(1,1-Dioxo-4-a,5,6,7,8,8a-hexahydro-1H-1lambda6-benzo[1,4,3]oxathiazin-3-ylamino)cyclopentanol (1,1-Dioxo-4-a,5,6,7,8,8a-hexahydro-1H-1lambda6-benzo[1,4,3]oxathiazin-3-yl)-(3,3,5,5-tetramethyl-cyclohexyl)amine (1,1-Dioxo-4-a,5,6,7,8,8a-hexahydro-1H-1lambda6-benzo[1,4,3]oxathiazin-3-yl)-((1R,2S,4R)-1,7,7-trimethylbicyclo[2.2.1]hept-2-yl)amine (1R,2S,3 S,4S)-3-(1,1-Dioxo-4-a,5,6,7,8,8a-hexahydro-1H-1lambda6-benzo[1,4,3]oxathiazin-3-ylamino)-1,7,7-trimethylbicyclo[2.2.1]heptan-2-ol Dicyclopropylmethyl-(1,1-dioxo-4-a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-(2,2,6,6-tetramethylpiperidin-4-yl)amine 3-(1,1-Dioxo-4-a,5,6,7,8,8a-hexahydro-1H-1lambda6-benzo[1,4,3]oxathiazin-3-ylamino)-7,7-dimethylbicyclo[2.2.1]heptan-2-ol 3-(1,1-Dioxo-4-a,5,6,7,8,8a-hexahydro-1H-1lambda6-benzo[1,4,3]oxathiazin-3-ylamino)-7-cyclopropylbicyclo[2.2.1]heptan-2-ol 4-(1,1-Dioxo-4-a,5,6,7,8,8a-hexahydro-1H-1lambda6-benzo[1,4,3]oxathiazin-3-ylamino)cyclohexanol 1-[(1,1-Dioxo-4-a,5,6,7,8,8a-hexahydro-1H-1lambda6-benzo[1,4,3]oxathiazin-3-ylamino)methyl]cyclohexanol (1R,2R,3 S,4S)-3-(1,1-Dioxo-4-a,5,6,7,8,8a-hexahydro-1H-1lambda6-benzo[1,4,3]oxathiazin-3-ylamino)bicyclo[2.2.1]heptane-2-carboxylic acid amide (1R,2R,3 S,4S)-3-(1,1-Dioxo-4-a,5,6,7,8,8a-hexahydro-1H-1lambda6-benzo[1,4,3]oxathiazin-3-ylamino)-bicyclo[2.2.1]heptane-2-carboxylic acid amide (1,1-Dioxo-4-a,5,6,7,8,8a-hexahydro-1H-1lambda6-benzo[1,4,3]oxathiazin-3-yl)-(tetrahydropyran-2-ylmethyl)amine (1,1-Dioxo-4-a,5,6,7,8,8a-hexahydro-1H-1lambda6-benzo[1,4,3]oxathiazin-3-yl)thiochroman-4-ylamine

[2-(1,1-Dioxo-4a,5,6,7,8,8a-hexahydro-1H-1lambda6-benzo[1,4,3]oxathiazin-3-ylamino)-2-methylcyclopentyl]methanol Cycloheptyl-((4aS,8aR)-1,1-dioxo-4-a,5,6,7,8,8a-hexahydro-1H-1lambda6-benzo[1,4,3]oxathiazin-3-yl)amine Cycloheptyl-((4aR,8aS)-1,1-dioxo-4a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-((1S,4R,5R)-1-isopropyl-4-methylbicyclo[3.1.0]hex-3-yl)amine (1R,5R)-Bicyclo[3.2.1]oct-2-yl-(1,1-dioxo-4-a,5,6,7,8,8a-hexahydro-1H-1lambda6-benzo[1,4,3]oxathiazin-3-yl)amine (1,1-Dioxo-4a,5,6,7,8,8a-hexahydro-1H-1lambda6-benzo[1,4,3]oxathiazin-3-yl)-(1-isobutyl-3-methylbutyl)amine (1,1-Dioxo-4a, 5,6,7,8,8a-hexahydro-1H-1lambda6-benzo[1,4,3]oxathiazin-3-yl)-((1S,2S, 3 S,5R)-2,6,6-trimethylbicyclo[3.1.1]hept-3-yl)amine (4,4-Difluorocyclohexyl)-(1,1-dioxo-4-a,5,6,7,8,8a-hexahydro-1H-1lambda6-benzo[1,4,3]oxathiazin-3-yl)amine ((4aS,8aR)-1,1-Dioxo-4-a,5,6,7,8,8a-hexahydro-1H-1lambda6-benzo[1,4,3]oxathiazin-3-yl)-(4-pentylbicyclo[2.2.2]oct-1-yl)amine

[(1R,2R)-2-((4aS,8aR)-1,1-Dioxo-4-a,5,6,7,8,8a-hexahydro-1H-1lambda6-benzo[1,4,3]oxathiazin-3-ylamino)cyclohexyl]methanol (4,4-Dimethylcyclohexyl)-(1,1-dioxo-4-a,5,6,7,8,8a-hexahydro-1H-1lambda6-benzo[1,4,3]oxathiazin-3-yl)amine (1R,2R,4S)-Bicyclo[2.2.1]hept-2-yl-((5S,6R)-1,1-dioxo-4-a,5,6,7,8,8a-hexahydro-1H-1lambda6-benzo[1,4,3]oxathiazin-3-yl)amine (1,1-Dioxo-1,4-a,5,6,7,7a-hexahydro-1lambda6-cyclopenta[1,4,3]oxathiazin-3-yl)-(4-methylbicyclo[2.2.2]oct-1-yl)amine (1,1-Dioxo-4-a,5,6,7,8,8a-hexahydro-1H-1lambda6-benzo[1,4,3]oxathiazin-3-yl)-(hexahydrocyclopenta[c]pyrrol-2-yl)-amine Azepan-1-yl-(1,1-dioxo-4-a,5,6,7,8,8a-hexahydro-1H-1lambda6-benzo[1,4,3]oxathiazin-3-yl)amine (2,6-Dimethylpiperidin-1-yl)-(1,1-dioxo-4-a,5,6,7,8,8a-hexahydro-1H-1lambda6-benzo[1,4,3]oxathiazin-3-yl)-amine (1,1-Dioxo-4-a,5,6,7,8,8a-hexahydro-1H-1lambda6-benzo[1,4,3]oxathiazin-3-yl)-(4-fluorobicyclo[2.2.2]oct-1-yl)amine N-Cyclohexyl-N'-(1,1-dioxo-4-a,5,6,7,8,8a-hexahydro-1H-1lambda6-benzo[1,4,3]oxathiazin-3-yl)-N-methylhydrazine Bicyclo[2.2.2]oct-1-yl-(1,1-dioxo-1,4-a,5,6,7,7a-hexahydro-1lambda6-cyclopenta[1,4,3]oxathiazin-3-yl)amine ((4aS,8aR)-1,1-Dioxo-4-a,5,6,7,8,8a-hexahydro-1H-1lambda6-benzo[1,4,3]oxathiazin-3-yl)-(4-fluorobicyclo[2.2.2]oct-1-yl)amine*

((4aR,8aS)-1,1-Dioxo-4-a,5,6,7,8,8a-hexahydro-1H-1lambda6-benzo[1,4,3]oxathiazin-3-yl)-(4-fluorobicyclo[2.2.2]oct-1-yl)amine*

(+)-Bicyclo[2.2.2]oct-1-yl-(1,1-dioxo-4-a,5,6,7,8,8a-hexahydro-1H-1lambda6-benzo[1,4,3]oxathiazin-3-yl)amine*

4-(1,1-Dioxo-4-a,5,6,7,8,8a-hexahydro-1H-1lambda6-benzo[1,4,3]oxathiazin-3-ylamino)bicyclo[2.2.2]octan-1-ol (1,1-Dioxo-4-a,5,6,7,8,8a-hexahydro-1H-1lambda6-benzo[1,4,3]oxathiazin-3-yl)-((1S,3R,5R)-9-methyl-9-azabicyclo[3.3.1]non-3-yl)amine (2,3,4,5,6,7,8,9,10,11-Decaborabicyclo[8.1.1]dodec-1-yl)-(1,1-dioxo-4-a,5,6,7,8,8a-hexahydro-1H-1lambda6-benzo[1,4,3]oxathiazin-3-yl)amine (1,1-Dioxo-4-a,5,6,7,8,8a-hexahydro-1H-1lambda6-benzo[1,4,3]oxathiazin-3-yl)-(1-isopropyl-2-methyl-propyl)amine Cyclohexylmethyl-(1,1-dioxo-4-a,5,6,7,8,8a-hexahydro-1H-1lambda6-benzo[1,4,3]oxathiazin-3-yl)amine 4-(1,1-Dioxo-4-a,5,6,7,8,8a-hexahydro-1H-1lambda6-benzo[1,4,3]oxathiazin-3-ylamino)cyclohexanol (−)-Bicyclo[2.2.2]oct-1-yl-(1,1-dioxo-4-a,5,6,7,8,8a-hexahydro-1H-1lambda6-benzo[1,4,3]oxathiazin-3-yl)amine*

Cyclohexyl-(4a,8a-dimethyl-1,1-dioxo-4-a,5,6,7,8,8a-hexahydro-1H-1lambda6-benzo[1,4,3]oxathiazin-3-yl)amine \* isomerically pure compound \*\* trans 2-Chlorocyclohexanesulfonyl isocyanate

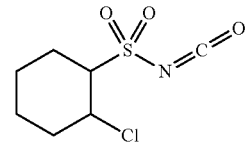 [SMILES: O=C=NS(=O)(=O)C1CCCCC1Cl]

Chemische Berichte 1970, 103(3), 663-669

2-Chlorocyclopentanesulfonyl isocyanate was prepared analogously:

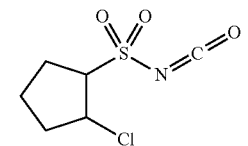 [SMILES: O=C=NS(=O)(=O)C1CCCC1Cl]

1-Isobutyl-3-methylbutylamine was prepared analogously:

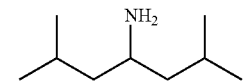

1-Isopropyl-2-methyl-propylamine

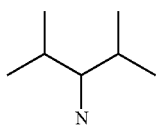

2,4-Dimethyl-3-pentanone (5 g) and titanium(IV) isopropoxide (24 g) were stirred in 7 N methanolic ammonia solution (30 ml) at room temperature for 5 hours. Sodium borohydride (2.5 g) was added while cooling the solution, and the mixture was stirred at room temperature for a further 2 hours. Subsequently, 10 N ammonium hydroxide solution (5 ml) was added, the mixture was filtered, and then 2 N hydrochloric acid (pH<2) was added to the solution. The solution was washed with ethyl acetate and then concentrated to dryness. This gave the hydrochloride of the product with a molecular weight of 115.2 g/mol ($C_7H_{17}N$), MS (ESI): m/e=116 (M+H+)

4-Pentylbicyclo[2.2.2]oct-1-ylamine

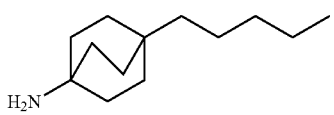

1.00 g of 4-pentylbicyclo[2.2.2]octane-1-carboxylic acid was dissolved in a mixture of 20 ml of toluen and 0.81 ml of N,N-diisopropylamine under an argon atmosphere, and then 1.06 ml of diphenylphosphoryl azide were added dropwise. After stirring at 100° C. for 2 hours and cooling to room temperature, the solvent was removed under reduced pressure. The residue was taken up in dichloromethane and washed with 5% aqueous citric acid and saturated aqueous sodium hydrogencarbonate solution, the organic phase was dried and the solvent was removed under reduced pressure. The crude product was purified by means of normal phase chromatography using a Flashmaster with an n-heptane/ethyl acetate gradient. The product-containing fractions were combined and concentrated by rotary evaporation. This gave the product (406 mg) with a molecular weight of 221.4 g/mol ($C_{14}H_{23}NO$).

390 mg of 1-isocyanato-4-pentylbicyclo[2.2.2]octane were suspended in 10 ml of aqueous 6 N hydrochloric acid and stirred at 100° C. over the course of 16 h. After cooling to room temperature, the precipitate was filtered off with suction and then dried by coevaporation with toluene under reduced pressure. The product (305 mg) with a molecular weight of 195.4 g/mol ($C_{13}H_{25}N$); MS (ESI): m/e=196 (M+H+) was obtained in the form of a hydrochloride salt.

3-Acetyl-5-chlorooxazolidin-2-one

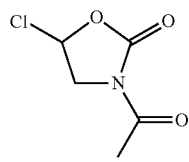

5.00 g of 3-acetyloxazolidin-2-one were initially charged in 25 ml of carbon tetrachloride and heated to 70° C. under an argon atmosphere. Then, alternately, a solution of 3.46 ml of sulfuryl chloride in 5 ml of carbon tetrachloride and 0.10 g of 2,2'-azobis(2-methylpropionitrile) were added, and then the mixture was stirred at the same temperature for 2 hours. After cooling to room temperature, the clear solution was decanted off from the solid residues, and the solvent was removed under reduced pressure. This gave the product (6.80 g) with a molecular weight of 163.6 g/mol ($C_5H_6ClNO_3$).

3-Acetyl-3H-oxazol-2-one

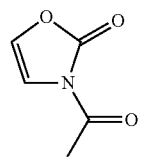

6.80 g of 3-acetyl-5-chlorooxazolidin-2-one were distilled in a Kugelrohr distillation under reduced pressure (50 mbar) at a temperature of 180° C. This gave the product (3.80 g) with a molecular weight of 127.1 g/mol ($C_5H_5NO_3$).

5-Acetyl-10-spirocyclopropyl-3-oxa-5-azatricyclo [5.2.1.0<2,6>]dec-8-en-4-one

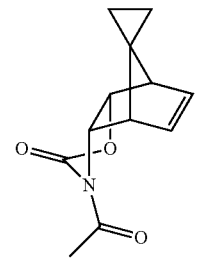 [SMILES: CC(=O)N1C(=O)OC2C1C1C=CC2C12CC2]

A vial containing 3.00 g of 3-acetyl-3H-oxazol-2-one and 2.89 ml of spiro[2.4]hepta-4,6-diene in 6 ml of 1,2-dichloroethane was closed with a Teflon septum and stirred at 200° C. in a microwave (Emrys Optimizer, Personal Chemistry) for 90 minutes. Subsequently, the solvent was removed under reduced pressure and the residue was purified twice by means of normal phase chromatography using a Flashmaster with an n-heptane/ethyl acetate gradient. The product-containing fractions were combined and concentrated by rotary evaporation. This gave the product (3.27 g) with a molecular weight of 219.2 g/mol ($C_{12}H_{13}NO_3$); MS (ESI): m/e=220 (M+H+).

5-Acetyl-10-spirocyclopropyl-3-oxa-5-azatricyclo [5.2.1.0<2,6>]decan-4-one

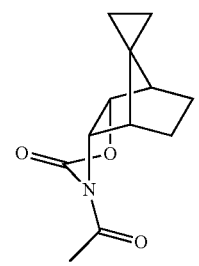 [SMILES: CC(=O)N1C(=O)OC2C1C1CCC2C12CC2]

1.50 g of 5-acetyl-10-spirocyclopropyl-3-oxa-5-azatricyclo[5.2.1.0<2,6>]dec-8-en-4-one were dissolved in 30 ml of ethanol and, with addition of 0.15 g of 5% Pd/C, stirred under a gauge hydrogen pressure of 0.5 bar for 1 hour. After filtration to remove the solid residues, the filtrate was freed of the solvent under reduced pressure.

This gave the product (1.47 g) with a molecular weight of 221.3 g/mol ($C_{12}H_{15}NO_3$); MS (ESI): m/e=222 (M+H+).

3-Amino-7-spiro-cyclopropylbicyclo[2.2.1]heptan-2-ol

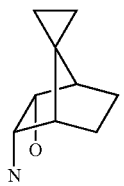 [SMILES: NC1C(O)C2CCC1C21CC1]

In a microwave vial, 1.86 g of potassium hydroxide were dissolved in 4 ml of water, and a solution of 1.47 g of 5-acetyl-10-spirocyclopropyl-3-oxa-5-azatricyclo[5.2.1.0<2,6>]decan-4-one in 2 ml of ethanol was added. After closure of the vial with a Teflon septum, the reaction mixture was stirred at 120° C. in a microwave (Emrys Optimizer, Personal Chemistry) for 90 minutes. Subsequently, the solvent was removed under reduced pressure and the residue was partitioned between ethyl acetate and water. The aqueous phase was washed twice with 50 ml of ethyl acetate and the combined organic phases were dried with sodium sulfate and the solvent was removed under reduced pressure.

This gave the product (930 mg) with a molecular weight of 153.2 g/mol ($C_9H_{15}NO$); MS (ESI): m/e=154 (M+H+).

5-Acetyl-10,10-dimethyl-3-oxa-5-azatricyclo[5.2.1.0*2,6*]decan-4-one

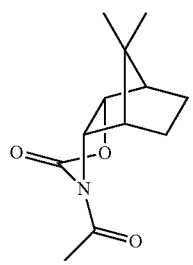 [SMILES: CC(=O)N1C(=O)OC2C1C1CCC2C1(C)C]

1.75 g of 5-acetyl-10-spiro-cyclopropyl-3-oxa-5-azatricyclo[5.2.1.0<2,6>]decan-4-one were dissolved in 20 ml of glacial acetic acid and, with addition of 0.33 g of platinum dioxide, stirred under a gauge hydrogen pressure of 0.5 bar for 16 hours. After filtration to remove the solid residues, the filtrate was freed of the solvent under reduced pressure. This gave the product (1.62 g) with a molecular weight of 223.3 g/mol ($C_{12}H_{17}NO_3$); MS (ESI): m/e=224 (M+H+).

3-Amino-7,7-dimethylcyclopropylbicyclo[2.2.1]heptan-2-ol

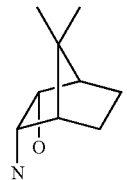

In a microwave vial, 2.04 g of potassium hydroxide were dissolved in 4 ml of water, and a solution of 1.62 g of 5-acetyl-10,10-dimethyl-3-oxa-5-azatricyclo[5.2.1.0*2,6*]decan-4-one in 2 ml of ethanol was added. After closure of the vial with a Teflon septum, the reaction mixture was stirred at 120° C. in a microwave (Emrys Optimizer, Personal Chemistry) for 90 minutes. Subsequently, the solvent was removed under reduced pressure and the residue was partitioned between ethyl acetate and water. The aqueous phase was washed twice with 50 ml of ethyl acetate and the combined organic phases were dried with sodium sulfate and the solvent was removed under reduced pressure.

This gave the product (920 mg) with a molecular weight of 155.2 g/mol ($C_9H_{17}NO$); MS (ESI): m/e=156 (M+H+).

Adamantan-1-ylhydrazine

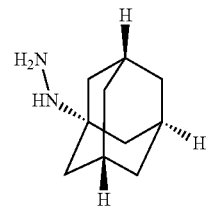

Helvetica Chimica Acta 1967, 50(7), 2008-2010

Amino-p-carborane

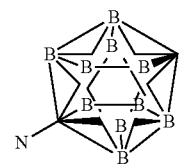

Inorganic Chemistry 1999, 38(12), 2936-2940

Sulfamoyl chloride

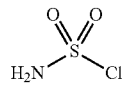

Journal of the American Chemical Society 1962, 94, 1994

N-Sulfinyl-4-toluamide

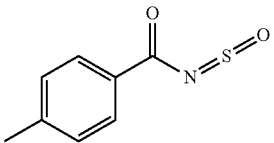

10 g of p-toluamide were suspended in 100 ml of ether and 12.5 ml of pyridine under argon. The 5.8 ml of thionyl chloride dissolved in 10 ml of ether were added dropwise at 5° C. and the mixture was stirred for a further 5 minutes. Subsequently, the cooling was removed and the mixture was stirred at room temperature for a further 16 hours. Under argon, the solid pyridinium hydrochloride was then filtered off, and then the solution was concentrated. The residue was used without further workup.

4a,8a-Dimethyl-3-p-tolyl-4-a,5,6,7,8,8a-hexahydrobenzo[1,4,3]oxathiazine 1-oxide

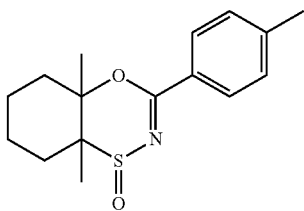 [SMILES: Cc1ccc(C2=NS(=O)C3(C)CCCCC3(C)O2)cc1]

The 3.17 g of N-sulfinyl-4-toluamide were dissolved in 20 ml of dry dichloromethane, and 3.85 g of 1,2-dimethylcyclohexene were slowly added dropwise at 5° C. After 16 hours, the mixture was concentrated under reduced pressure and chromatographed using silica gel. This gave the product (1.57 g) with a molecular weight of 291.4 g/mol ($C_{16}H_{21}NO_2S$); MS (ESI): m/e=292 (M+H+)

4a,8a-Dimethyl-3-p-tolyl-4-a,5,6,7,8,8a-hexahydrobenzo[1,4,3]oxathiazine 1,1-dioxide

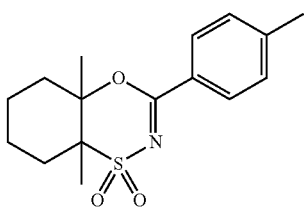 [SMILES: Cc1ccc(C2=NS(=O)(=O)C3(C)CCCCC3(C)O2)cc1]

228 mg of 4a,8a-dimethyl-3-p-tolyl-4-a,5,6,7,8,8a-hexahydrobenzo[1,4,3]oxathiazine 1-oxide were dissolved in 4 ml of dichloromethane, and 190 mg of m-chloroperbenzoic acid were added at 5° C. and the mixture was stirred for 16 hours. The m-chlorobenzoic acid formed was filtered off and the filtrate was washed twice with 0.1 N aqueous NaOH solution and once with saturated NaCl solution, dried with sodium sulfate, filtered and concentrated. The residue was recrystallized from n-pentane/diethyl, ether. This gave the product (128 mg) with a molecular weight of 307.4 g/mol ($C_{16}H_{27}NO_3S$); MS (ESI): m/e=308 (M+H+)

2-Hydroxy-1,2-dimethylcyclohexanesulfonamide

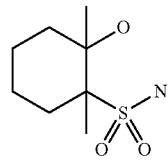

137 mg of 4a,8a-dimethyl-3-p-tolyl-4-a,5,6,7,8,8a-hexahydrobenzo[1,4,3]oxathiazine 1,1-dioxide were dissolved in methanol, 1.5 ml of 6 N NaOH were added and the mixture was boiled overnight. After cooling, the mixture was acidified with concentrated hydrochloric acid and the methanol was evaporated off under reduced pressure. The residue was then admixed with 10 ml of water and extracted twice with 10 ml of n-butanol. The n-butanol was evaporated under reduced pressure and the residue (96 mg) was used without further workup.

4-(3,6-Dihydro-2H-pyran-4-yl)morpholine

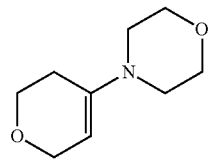 [SMILES: C1=C(N2CCOCC2)CCOC1]

650 mg of tetrahydro-4H-pyran-4-one together with 950 mg of morpholine were dissolved in 10 ml of toluene and the mixture was heated under reflux in a light water separator for 5 hours. Subsequently, the mixture was concentrated under reduced pressure, and residue (1.3 g) was used further without further workup.

4-Oxotetrahydropyran-3-sulfonamide

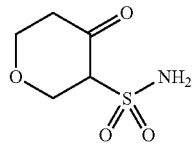 [SMILES: NS(=O)(=O)C1COCCC1=O]

1.3 g of 4-(3,6-dihydro-2H-pyran-4-yl)morpholine were dissolved under argon in 12 ml of THF, the mixture was cooled to −40° C., and then 1.3 g of sulfamoyl chloride were added, followed by 6 ml of diisopropylamine. The cooling was removed and, after the mixture had come to room temperature, it was stirred for another 2 hours. An oil separated out. The THF was decanted off, and the residue was taken up in methanol and filtered through silica gel. The filtrate was concentrated under reduced pressure and the residue, bound to 12 g of Celite, was purified by means of a silica gel column (50 g): solvent A: dichloromethane, B: methanol, gradient: 0 min 2% B, 3 min 2% B, 5 min 5% B, 35 min 10% B, 45 min 10% B; flow rate 20 ml/min; detection: 220 nm, fraction size: 20 ml. After removal of the solvent under reduced pressure, the product was thus obtained with impurities. The residue (1.09 g) was used further without further workup.

4-Hydroxytetrahydropyran-3-sulfonamide

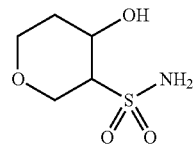 [SMILES: NS(=O)(=O)C1COCCC1O]

1.09 g of 4-oxotetrahydropyran-3-sulfonamide were dissolved in THF, 0.23 g of sodium borohydride was added and the mixture was stirred at room temperature for 18 hours. The mixture was then adjusted to pH=2 with hydrochloric acid and concentrated under reduced pressure. The residue, bound to 8 g of Celite, was purified by means of a silica gel column (50 g): solvent A: dichloromethane, B: methanol, gradient: 0 min 3% B, 3 min 3% B, 5 min 5% B, 35 min 10% B, 44 min 10% B; flow rate 20 ml/min; detection: 220 nm, fraction size: 20 ml. After removal of the solvent under reduced pressure, the product was thus obtained with impurities. The residue (615 mg) was used further without further workup.

Cyclohexyl-(4a,8a-dimethyl-1,1-dioxo-4-a,5,6,7,8, 8a-hexahydro-1H-1lambda6-benzo[1,4,3]oxathiazin-3-yl)amine

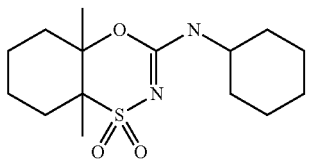 [SMILES: CC12CCCCC1(C)S(=O)(=O)N=C(NC1CCCCC1)O2]

90 mg of 2-hydroxy-1,2-dimethylcyclohexanesulfonamide were suspended in DMF and then treated with 54 mg of potassium tert-butoxide in an ultrasound bath for 5 minutes. Then 67 mg of cyclohexyl isothiocyanate were added. After stirring for 3 minutes, 68 mg of N-bromosuccinimide were then added and the mixture was stirred for a further 5 minutes. The solution was then concentrated under reduced pressure and purified by preparative HPLC. This gave the product (3.4 mg) with a molecular weight of 314.4 g/mol; MS (ESI) m/e=315 (M+H+).

The following products were prepared in the same way:
trans-Cyclohexyl-(1,1-dioxo-5,6,8,8a-tetrahydro-1H,4aH-4, 7-dioxa-1lambda*6*-thia-2-azanaphthalen-3-yl)amine

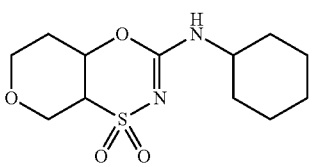 [SMILES: O=S1(=O)N=C(NC2CCCCC2)OC2CCOCC21]

cis-Cyclohexyl-(1,1-dioxo-5,6,8,8a-tetrahydro-1H,4aH-4,7-dioxa-1lambda*6*-thia-2-azanaphthalen-3-yl)amine

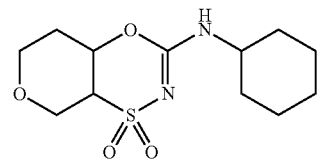 [SMILES: O=S1(=O)N=C(NC2CCCCC2)OC2CCOCC21]

Cyclohexyl-(1,1-dioxo-4-a,5,6,7,8,8a-hexahydro-1H-1lambda*6*-benzo[1,4,3]oxathiazin-3-yl)amine

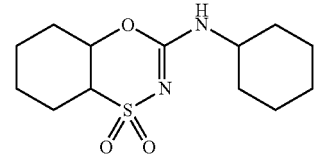 [SMILES: O=S1(=O)N=C(NC2CCCCC2)OC2CCCCC21]

The trans-cyclohexyl-(1,1-dioxo-5,6,8,8a-tetrahydro-1H, 4aH-4,7-dioxa-1lambda*6*-thia-2-azanaphthalen-3-yl) amines were obtained by separation on a chiral column (see table 1).

Cyclohexyl-(7,7-difluoro-1,1-dioxo-4-a,5,6,7,8,8a-hexahydro-1H-1lambda*6*-benzo[1,4,3]oxathiazin-3-yl)amine

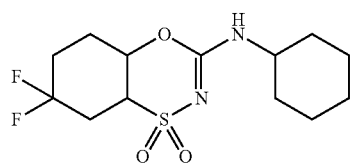 [SMILES: O=S1(=O)N=C(NC2CCCCC2)OC2CCC(F)(F)CC21]

3-(2-Fluorophenoxy)-4-a-methyl-4-a,5,6,7,8,8a-hexahydrobenzo[1,4,3]oxathiazine 1,1-dioxide

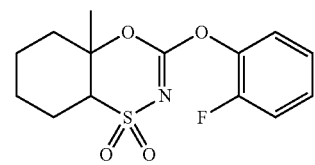 [SMILES: CC12CCCCC1S(=O)(=O)N=C(Oc1ccccc1F)O2]

6.42 g of chlorosulfonyl isocyanate were dissolved in 65 ml of methylene chloride, and 6.7 g of 2-fluorophenol were added at room temperature. After 1 hour, the mixture was concentrated under reduced pressure, and the residue was dissolved in 30 ml of THF and cooled to −78° C. 1.95 g of 60% sodium hydride were added to this solution and the cooling was removed. Subsequently, the mixture was heated gradually to 35° C. and then 1-methyl-1-cyclohexene was added. The mixture was stirred at 35° C. for another 2 hours and then poured onto 100 g of ice. The mixture was extracted with ethyl acetate, dried with sodium sulfate, filtered and concentrated under reduced pressure. The crude product was used further without further purification.

Cyclohexyl-(4a-methyl-1,1-dioxo-4-a,5,6,7,8,8a-hexahydro-1H-1lambda*6*-benzo[1,4,3]oxathiazin-3-yl)amine

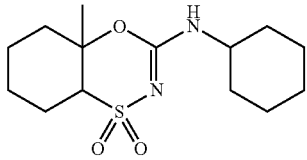

1 g of 3-(2-fluorophenoxy)-4-a-methyl-4-a,5,6,7,8,8a-hexahydrobenzo[1,4,3]oxathiazine 1,1-dioxide was dissolved in methylene chloride, 320 mg of cyclohexylamine and 412 mg of diisopropylamine were added, and the mixture was stirred at room temperature overnight. The solution was then concentrated under reduced pressure and purified by preparative HPLC. This gave the product (20 mg) with a molecular weight of 300.4 g/mol; MS (ESI) m/e=301 (M+H+)

The invention claimed is:

1. A compound of the formula I

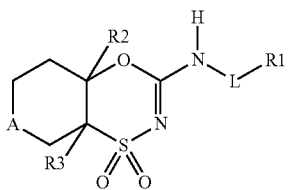

in which

A is a bond, $CH_2$, $CF_2$, O;

L is a bond, C(R5)(R6), N(R5);

R1 ($C_3$-$C_8$)-carbocycle,
  where the carbocycle radical may be mono- to trisubstituted by F, Cl, Br, I, OH, —($C_1$-$C_6$)-alkylene-OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

($C_6$-$C_{10}$)-aryl,
  where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

4-12-membered heterocycle,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—N(($C_1$-$C_6$)-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

and where the heterocycle may be fused to a further ring or ring system;

R2, R3 are each independently H, ($C_1$-$C_6$)-alkyl;

R5, R6 are each independently H, ($C_1$-$C_6$)-alkyl, ($C_3$-$C_8$)-cycloalkyl, $(C(R7)(R8))_n$—O—(CO)—N(R7)(R8);

R7, R8 are each independently H, ($C_1$-$C_6$)-alkyl;

n is 0, 1, 2;

and pharmaceutically acceptable salts thereof.

2. The compound of claim 1, wherein

A is a bond, $CH_2$, $CF_2$;

L is a bond, C(R5)(R6), N(R5);

R1 ($C_3$-$C_8$)-carbocycle,
  where the carbocycle radical may be mono- to trisubstituted by F, Cl, Br, I, OH, —($C_1$-$C_6$)-alkylene-OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH_2$, ($C_1$-$C_6$)-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

a heterocycle selected from the group of thiophene, pyran, tetrahydropyran, piperidine, thiopyran, tetrahydrothiopyran, pyrrole, tetrahydropyrrole, azepane or 2,3,4,5,6,7,8,9,10,11-decabora-bicyclo[8.1.1]dodecane,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH_2$, ($C_1$-$C_6$)-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

and where the heterocycle may be fused to a further ring or ring system;

R2, R3 are each independently H, ($C_1$-$C_6$)-alkyl;

R5, R6 are each independently H, ($C_1$-$C_6$)-alkyl, ($C_3$-$C_8$)-cycloalkyl, ($C_1$-$C_6$)-alkylene-($C_3$-$C_8$)-cycloalkylene, $(C(R7)(R8))_n$—O—(CO)—N(R7)(R8);

R7, R8 are each independently H, ($C_1$-$C_6$)-alkyl;

n is 0, 1, 2;

and pharmaceutically acceptable salts thereof.

3. The compound of claim 1, wherein

A is a bond, $CH_2$, $CF_2$;

L is a bond, C(R5)(R6), N(R5);

R1 ($C_3$-$C_8$)-carbocycle,
  where the carbocycle radical may be mono- to trisubstituted by F, Cl, Br, I, OH, —($C_1$-$C_6$)-alkylene-OH, $CF_3$, $NO_2$, CN, $OCF_3$, ($C_1$-$C_6$)-alkyl, $CONH_2$, $CONH(C_1$-$C_6)$-alkyl, $CON((C_1$-$C_6)$-alkyl$)_2$;

phenyl,
  where the phenyl radical may be mono- to trisubstituted by F, Cl, Br, I, OH, —($C_1$-$C_6$)-alkylene-OH, $CF_3$, $NO_2$, CN, $OCF_3$, ($C_1$-$C_6$)-alkyl, $CONH_2$, $CONH(C_1$-$C_6)$-alkyl, $CON((C_1$-$C_6)$-alkyl$)_2$;

a heterocycle selected from the group of carborane, thiophene, tetrahydropyran, piperidine, thiochromane, hexahydrocyclopenta[c]pyrrole, azepane and 2,3,4,5,6,7,8,9,10,11-decaborabicyclo[8.1.1]dodecane, where the heterocycle radical may be mono- to trisubstituted by F, Cl, Br, I, OH, —($C_1$-$C_6$)-alkylene-OH, $CF_3$, $NO_2$, CN, $OCF_3$, ($C_1$-$C_6$)-alkyl, $CONH_2$, CONH($C_1$-$C_6$)-alkyl, CON(($C_1$-$C_6$)-alkyl)$_2$;

R2, R3 are each independently H, ($C_1$-$C_6$)-alkyl;
R5, R6 are each independently H, ($C_1$-$C_6$)-alkyl;
and pharmaceutically acceptable salts thereof.

4. A pharmaceutical composition comprising the compound of claim 1, or pharmaceutically acceptable salts thereof, and a pharmaceutically acceptable carrier and/or excipient.

5. The pharmaceutical composition of claim 4, further comprising at least one further active ingredient.

6. The pharmaceutical composition of claim 5, wherein said active ingredient is one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TRβ agonists or amphetamines.

7. A process for preparing a pharmaceutical composition comprising mixing the compound of claim 1 with a pharmaceutically suitable carrier and converting said mixture to a form suitable for administration.

8. A method of treating hyperglycemia comprising administering to a patient in need thereof a therapeutically effective amount of the pharmaceutical composition of claim 4.

9. A method of treating diabetes comprising administering to a patient in need thereof a therapeutically effective amount of the pharmaceutical composition of claim 4.

10. A method of treating insulin resistance comprising administering to a patient in need thereof a therapeutically effective amount of the pharmaceutical composition of claim 4.

11. A kit consisting of separate packages of
a) an effective amount the compound of claim 1 and
b) an effective amount of a further active medicament ingredient.

* * * * *